(12) United States Patent
O'Connor

(10) Patent No.: US 7,588,758 B2
(45) Date of Patent: Sep. 15, 2009

(54) COX-2 FUNCTION AND WOUND HEALING

(75) Inventor: J. Patrick O'Connor, Fanwood, NJ (US)

(73) Assignee: University of Medicine and Dentistry of New Jersey, Somerset, NJ (US)

( * ) Notice: Subject to any disclaimer, the term of this patent is extended or adjusted under 35 U.S.C. 154(b) by 0 days.

(21) Appl. No.: 09/953,067

(22) Filed: Sep. 11, 2001

(65) Prior Publication Data

US 2003/0082141 A1    May 1, 2003

(51) Int. Cl.
*A61K 38/44* (2006.01)
*C12N 9/02* (2006.01)
*C12P 21/04* (2006.01)
*C12N 1/20* (2006.01)
*C07H 21/04* (2006.01)

(52) U.S. Cl. .............. 424/94.4; 435/189; 435/69.1; 435/71.1; 435/252.3; 536/23.2

(58) Field of Classification Search .......... 435/190, 435/325, 189, 440, 25, 4, 6; 424/94.9, 94.4; 536/23.2, 23.5; 533/23.5
See application file for complete search history.

(56) References Cited

U.S. PATENT DOCUMENTS 6,638,744 B2 * 10/2003 Wisnewski et al. .......... 435/189
2002/0064845 A1 * 5/2002 Wisnewski et al. .......... 435/183

OTHER PUBLICATIONS

Okada et al. Prostaglandin G?H syntahse-2 is required for maximal formation of oxteoclast-like cells in culture. The J. of Clini Investigation. vol. 105, No. 6, pp. 823-832. Mar. 2000.*
Forwood et al. Inducible cyclo-oxygenase (COX-2) mediates the induction of bone formation by mechanical loading in vivo. Journal of Bone and Mineral Research. vol. 11, No. 11, pp. 1688-1693. 1996.*
BRENDA database—Entry of prostaglandin-endoperoxide synthase.*
Rys-Sikora et al. Coordinate expression of secretory phospholipase A(2) and cyclooxygenase-2 in activated human keratinocytes.Am J Physiol Cell Physiol. Apr. 2000;278(4):C822-33.*
Sato et al. Expression of cyclooxygenase genes and involvement of endogenous prostaglandin during osteogenesis in the rat tibial bone marrow cavity.J Med Dent Sci. Dec. 1997;44(4):81-92.*
Funk et al. NCBI database—P23219.*
Jones et al. NCBI database—P35354.*
Jorgensen et al. Bone formation induced in an infant by systemic prostaglandin-E2 administration. Acta Orthop Scand. Aug. 1988;59(4):464-6.*
Akamine et al. Bone 13:11-22, 1992.*
Drvaric et al. Clin Orthop 246:300-304, 1989.*
Jee et al. Calcif Tissue Int 37:148-156, 1985.*
Hung, Jaou-Chen et al., Gene Transfer to Cultured Human Endometrial Stromal Cells: A Model to Study Cyclooxygenasa-2 Gene Regulation, *Fertility and Sterility*, vol. 70, No. 4, pp. 734-739, Oct. 1998.
McCormack, Keith, Roles of COX-1 and COX-2, *J. Rheumatology*, 25:11, p. 2279-2281 (1998).
Needleman, Philip, et al., The Discovery and Function of COX-2, *J. Rheumatology*, 24:49, p. 6-8 (1997).
Wu, Kenneth K., Injury-Coupled Induction of Endothelial eNOS and COX-2 Genes: A Paradigm for Thromboresistant Gene Therapy, *Proceedings of the Association of American Physicians*, 110:3, p. 163-170 (1998).
Rubin, Bernard R., "Osteoarthritis", JAOA 2001 Part 2 101 (4) :S2-S5.

* cited by examiner

*Primary Examiner*—Yong D Pak
(74) *Attorney, Agent, or Firm*—Licata & Tyrrell P.C.

(57) ABSTRACT

The invention relates to compositions and methods for enhancing bone healing, bone formation and wound healing. More specifically, it relates to the use of cyclooxygenase 2 (COX-2) following bone fracture, orthopaedic procedure or wound infliction to enhance healing.

12 Claims, 6 Drawing Sheets

Figure 1. Radiographic Analysis of Fracture Healing in COX2-Selective NSAID Treated Rats
A. Control
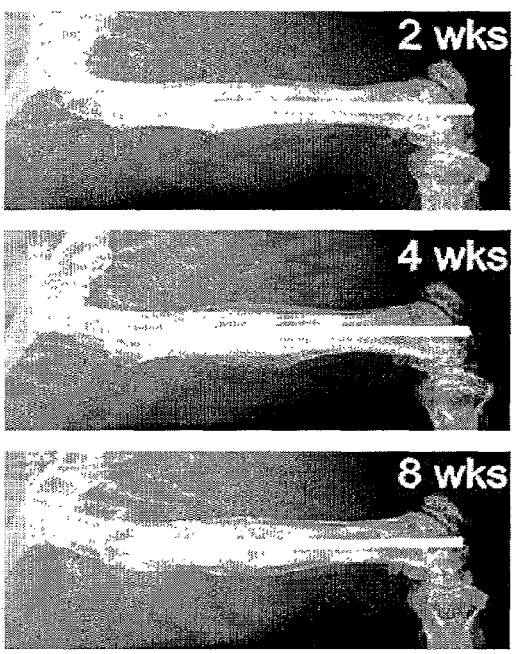
B. Indomethacin
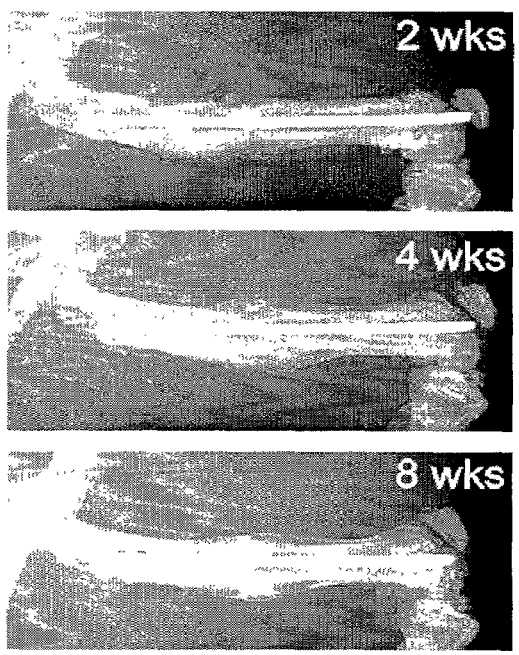
C. Celecoxib
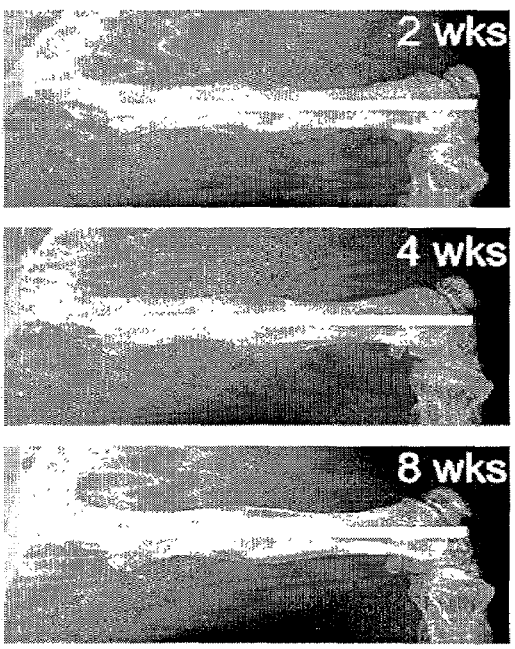
D. Rofecoxib
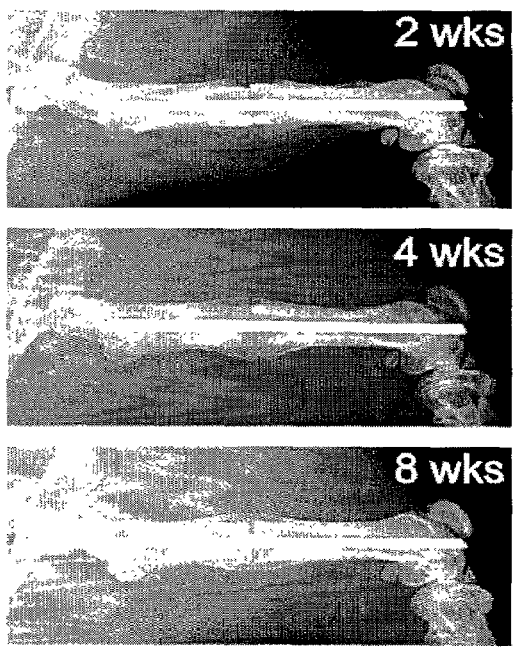
Radiographs were made using an HP Faxitron and Kodak MINR2000 film. Treatment groups and post-fracture time points are indicated.

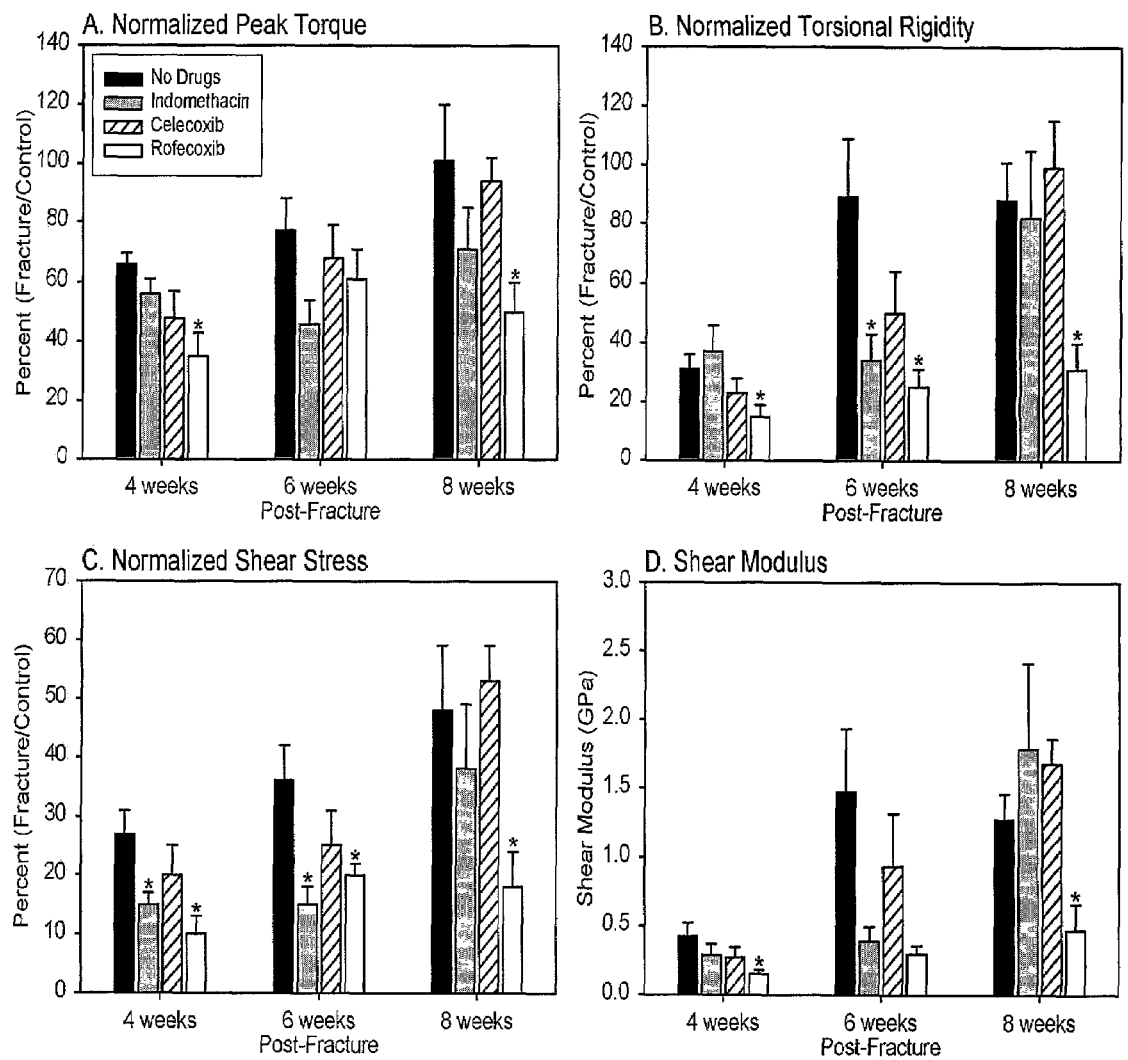
Figure 2. Rofecoxib Treatment Reduces Fracture Callus Mechanical Properties (* indicates P<0.05 as per t-test)

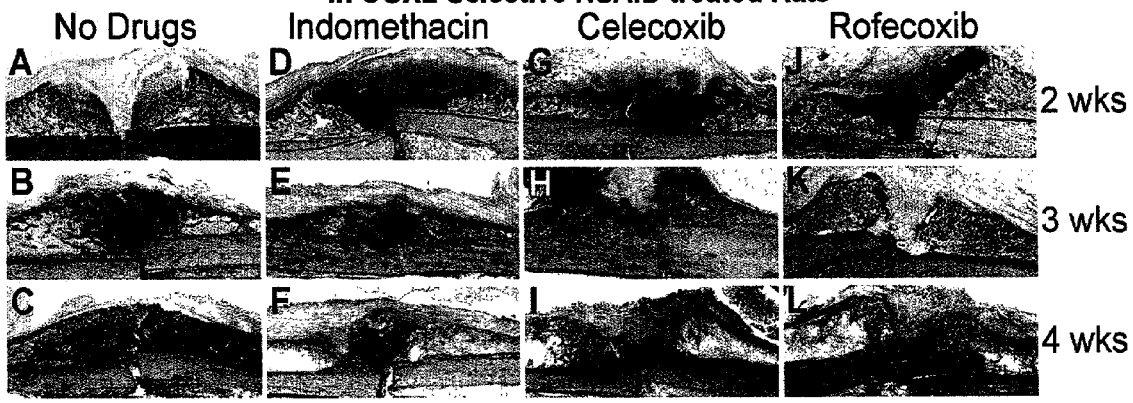

Figure 3. Endochondral Ossification Fails during Fracture Healing in COX2-Selective NSAID treated Rats Fractured femurs were fixed and embedded in PMMA. The specimens were sectioned sagitally through the fracture callus and stained with van Gieson's picrofuchsin and Stevenel's bue. Drug treatment and times post-fracture are indicated. Note the lack of chondrocytes and cartilage in the 3 and 4 week post-fracture celecoxib and rofecoxib treated specimens indicative of failed endochondral ossification.

Figure 4. Osteoclast activity (4-weeks post-fracture) on the cortical bone next to the fracture site in rofecoxib treated rats.
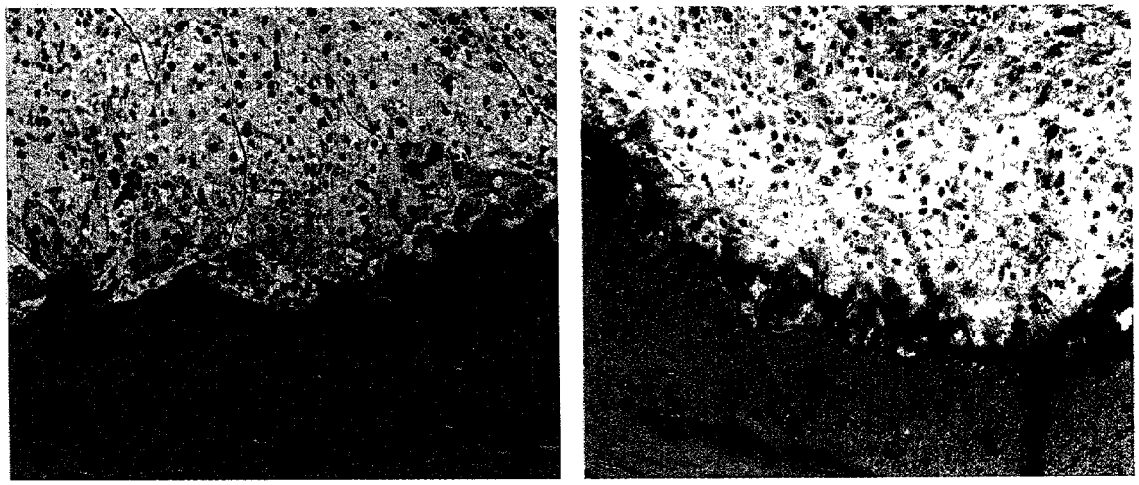

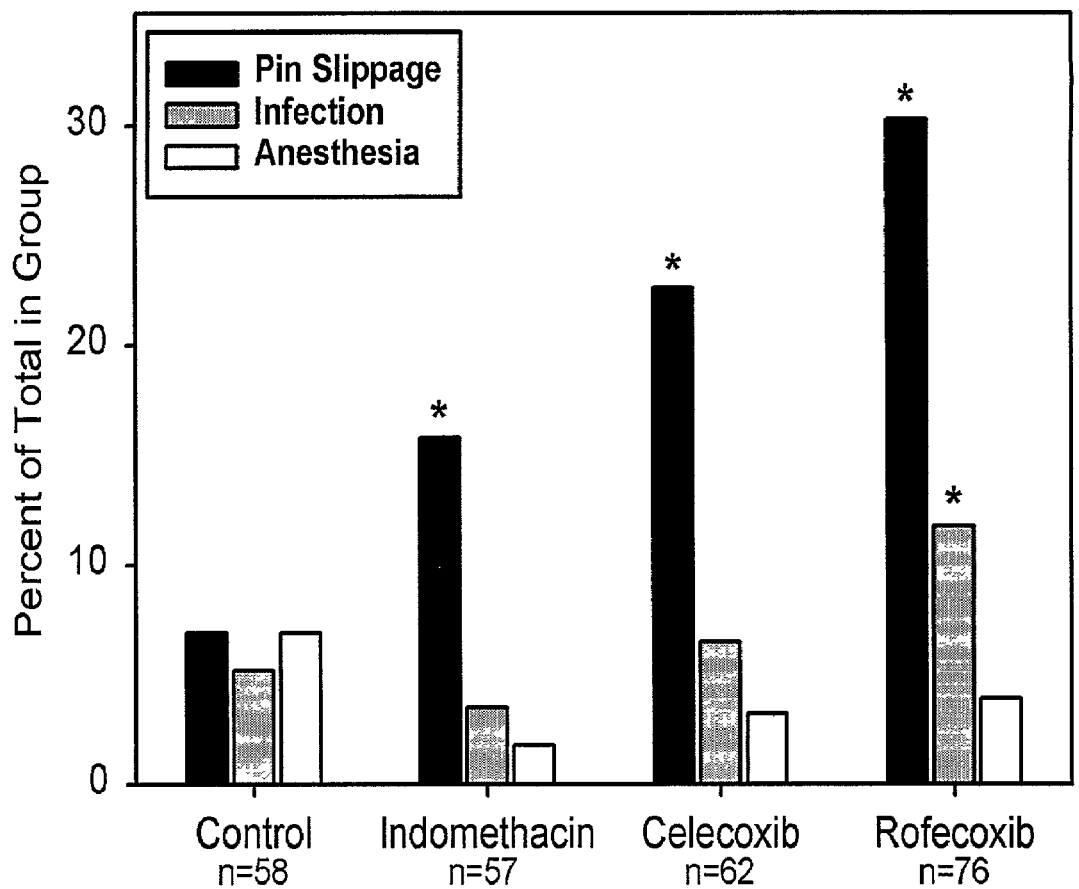
Figure 5. Complication Rates Associated with NSAID Treatment during Fracture Healing (* indicates $P<0.01$ based upon $\chi^2$)

Figure 6. Fracture Healing in Cox Knock-out Mice.

A. $Cox1^{-/-}$

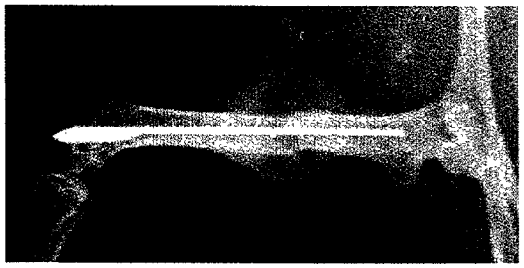

D. $Cox2^{-/-}$

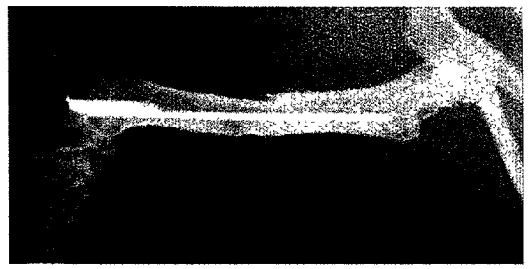

B. $Cox1^{-/-}$ (5X)

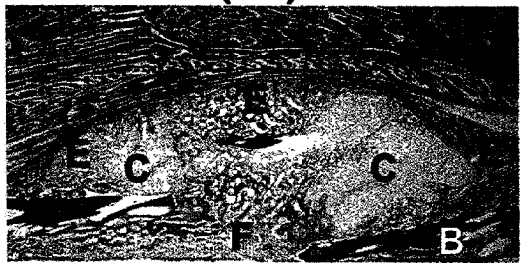

E. $Cox2^{-/-}$ (10X)

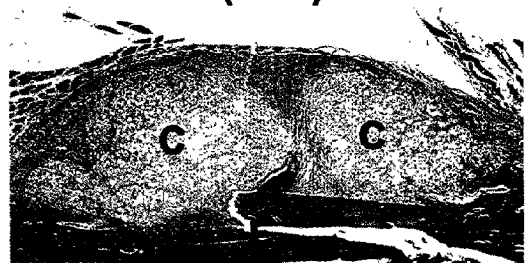

C. $Cox1^{-/-}$ (10X)

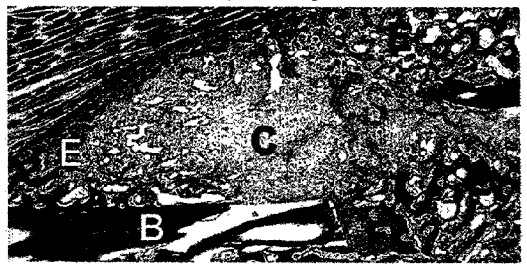

F. $Cox2^{-/-}$ (25X)

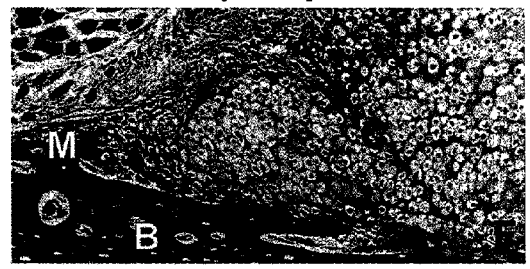

Mouse genotypes are indicated. Panels A and D. Radiographs of mouse femur fractures at 2 weeks post-fracture. Panels B, C, E, and F. Decalcified paraffin sections from the mouse fractures at 2 weeks post-fracture stained with Masson's trichrome. B=cortical bone; F= fracture site; C= chondrocytes and cartilage; E= area of endochondral ossification; M= intramembraneous bone formation. Original photographic magnification is indicated.

COX-2 FUNCTION AND WOUND HEALING

FIELD OF THE INVENTION

This invention relates to the field of cyclooxygenase activity and wound healing.

BACKGROUND OF THE INVENTION

Bones, along with a small number of cartilages, comprise the skeletal system that serves as the rigid supporting framework of the body in adult humans. Certain parts of the supporting framework form chambers, such as the skull and the thoracic cage, that are important for protecting the soft parts contained in the chambers. Bones also serve as attachments for muscles and act as levers in the joint system of the body.

Mature bone is comprised of an organic framework of fibrous tissue and inorganic salts known as crystalline hydroxyapatite (HA). HA is composed of calcium and phosphorous, which are derived from the blood plasma and ultimately from nutritional sources. HA represents about 60 percent of the weight of compact bone and is deposited on a fibrous structure of collagenous connective tissue. Without HA, bone loses most its weight and rigidity and is susceptible to damage.

The process of bone formation, also known as osteogenesis, involves three main steps: production of the extracellular organic matrix (osteoid); mineralization of the matrix to form bone; and bone remodeling by resorption and reformation. The cellular activities of osteoblasts, osteocytes, and osteoclasts are essential to the process.

Osteoblasts synthesize the collagenous precursors of bone matrix and also regulate its mineralization. During bone formation, osteoblasts line tiny spaces known as lacunae within the surrounding mineralized matrix. Osteoblasts that line the lacunae are called osteocytes. Osteocytes occupy minute canals (canaliculi) which permit the circulation of tissue fluids. Hormones, growth factors, physical activity, and other stimuli act mainly through osteoblasts to bring about effects on bone. Osteoclasts are derived from hematopoietic stem cells that also give rise to monocytes and macrophages. Osteoclasts adhere to the surface of bone undergoing resorption and lie in depressions referred to as resorption bays. Osteoclasts are apparently activated by signals from osteoblasts. Osteoclastic bone resorption does not occur in the absence of osteoblasts. To meet the requirements of skeletal growth and mechanical function, bone undergoes dynamic remodeling by a coupled process of bone resorption by osteoclasts and reformation by osteoblasts.

Bone is formed through one of two pathways, by replacement of cartilage or by direct elaboration from periosteum. These processes are known, respectively, as endochondral ossification and intramembranous ossification. During endochondral ossification, a cartilaginous bone model is first formed. Then, a layer of bone on the surface of the cartilaginous shaft is formed by osteoblasts. Succeeding layers of bone follow. At the same time, the matrix of cartilage cells is calcified into a trabecular network of cartilage while the interstitial cartilage is degenerated. The combined processes of calcification and degeneration of the cartilage advance from the center toward the ends of the cartilage model. The osteoblasts penetrate the cartilage along with capillaries to produce bone on the cartilaginous trabeculae and advance from the center to the ends to progressively form bone on the cartilaginous trabeculae. Ultimately, the calcified cartilage is completely replaced by spongy bone.

In contrast, the process of intramembranous ossification does not involve a cartilaginous template. Instead, mesenchymal cells become osteoblasts which begin to form the branching trabeculae of bone. The initial thin trabeculae are some times referred to as spicules. The trabecular bone becomes denser by widening of the trabeculae, and is then remodeled externally and internally. The mandibles, clavicles and certain bones of the skull are produced through intramembranous ossification.

There are a number of diseases related to bone formation, deterioration and healing, including osteoporosis, osteogenesis imperfecta (OI) and fibrodysplasia ossificans progressiva (FOP). Osteoporosis, or porous bone, is a disease characterized by low bone mass and structural deterioration of bone tissue, leading to bone fragility and an increased susceptibility to fractures of the hip, spine, and wrist. Osteoporosis is a major public health threat for more than 28 million Americans, 80 percent of whom are women. The strength of bone depends on its mass and density. Bone density depends in part on the amount of calcium, phosphorus and other minerals bones contain. Bones that contain less mineral are weakened and lose internal supporting structure. A full cycle of bone remodeling takes about 2 to 3 months. Children tend to make new bone faster than old bone is broken down. As a result, bone mass increases. Peak bone mass is reached in an individual's mid-30s. Although bone remodeling continues, old bone is broken down faster than new bone is formed. As a result, adults lose slightly more bone than is gained—about 0.3 percent to 0.5 percent a year. Lack of vitamin D and calcium in an individual's diet can accelerate the process. In addition, for women at menopause, estrogen levels drop and bone loss accelerates to about 1 percent to 3 percent a year. Bone loss slows but doesn't stop at around age 60. Women may lose between 35 percent and 50 percent of their bone mass, while men may lose 20 percent to 35 percent of their bone mass. Development of osteoporosis depends on the bone mass attained between ages 25 and 35 (peak bone mass) and how rapidly it is lost as an individual get older. The higher an individual's peak bone mass, the less likely that individual will develop osteoporosis. Calcium, vitamin D and exercising regularly are important for maintaining bone strength. Nonetheless, methods for effectively treating osteoporosis are still desired.

Osteogenesis Imperfecta (OI) is a genetic disorder characterized by bones that break easily, often from little or no apparent cause. There are at least four distinct forms of the disorder, representing extreme variation in severity from one individual to another. For example, a person may have as few as ten or as many as several hundred fractures in a lifetime. While the number of persons affected with OI in the United States is unknown, the best estimate suggests a minimum of 20,000 and possibly as many as 50,000. OI can be dominantly or recessively inherited and can also occur as a mutation. A cure for OI has not yet been discovered. As a result, methods for treatment focus on preventing and controlling symptoms, strengthening bone mass and ensuring proper healing.

In addition, both osteoporosis and OI leave patients vulnerable to bone fractures. If these bone fractures do not heal properly, these patients may continue to suffer from pain and may be at increased risk for further fractures as well as other related complications. Methods or treatments that enhance and/or ensure proper fracture healing are important for patients with osteoporosis or brittle bone disease. Another group that will benefit from methods for enhanced wound healing are the elderly and patients who have undergone orthopaedic procedures.

Fracture healing is the culmination of a highly orchestrated series of physiological and cellular pathways to restore the function of broken bones. Fracture healing generally involves the following steps: the formation of a hematoma (collection of blood at the fracture site), development of a soft callus due to cell multiplication in the lining of the injured bone, growth of blood vessels and fibrocartilege in the middle of the fracture, formation of osteoblasts that migrate into the callus and deposit calcium to form a hard callus, and remodeling and strengthening of the bone through osteoblast and osteoclast formation.

Osteogenesis during fracture healing occurs by intramembraneous and endochondral ossification that histologically resembles fetal skeletogenesis (Einhorn 1998; Vortkamp et al. 1998; Ferguson et al. 1999). However, the localized tissue hypoxia, the fracture hematoma, subsequent inflammation at the fracture site, and the frank remodeling of the fracture callus at the later stages of healing are unique physiological and cellular responses to bone fractures that have no known corresponding counterpart during fetal development of the skeleton.

It has been hypothesized that the early physiological responses to a bone fracture, namely hypoxia and inflammation, induce gene expression pathways and promote cell proliferation and migration into the fracture site in order to promote healing (Brighton et al. 1991; Bolander 1992). Production or release of specific growth factors, cytokines, and local hormones at the fracture site by these physiological processes would create the appropriate microenvironment to (1) stimulate periosteal osteoblast proliferation and intramembraneous ossification to form the hard fracture callus, (2) stimulate cell proliferation and migration into the fracture site to form the soft callus, and (3) stimulate chondrocyte differentiation in the soft callus with subsequent endochondral ossification. Remodeling of the fracture callus by osteoclastic resorption and subsequent osteogenesis converts the fracture callus woven bone into cortical bone and thereby restores the shape and mechanical integrity of the fractured bone.

One potential class of factors that would mediate certain events of fracture healing is the prostaglandins. The effects of prostaglandins on bone metabolism are complex since prostaglandins can stimulate bone formation as well as bone resorption (Kawaguchi et al. 1995). However, because the in vivo half-life of purified or synthetic prostaglandins is very short, prostaglandins per se have a limited therapeutic value.

Prostaglandins are synthesized by osteoblasts and different cell stimuli can alter the amount and possibly the spectrum of prostaglandins produced by osteoblasts (Feyen et al. 1984; Klein-Nulend et al. 1997; Wadleigh and Herschman 1999). Therefore, signal transduction, mechanical perturbations, or other physiological signals can affect bone metabolism through altercation of prostaglandin production.

Prostaglandin synthesis begins with the release of arachidonic acid from membrane phospholipids by phospholipase activity. Arachidonic acid is subsequently converted into prostaglandin $H_2$ ($PGH_2$) by cyclooxygenase (COX) via two independent catalytic steps (Needleman et al. 1986). Synthase enzymes then convert $PGH_2$ into the specific prostaglandins produced by that cell such as $PGD_2$, $PGE_2$, $PGF_{2\alpha}$, prostacyclin, and thromboxane. Thus, cyclooxygenase activity is essential for normal prostaglandin production and cyclooxygenase is believed to be the rate-limiting enzyme in the prostaglandin synthetic pathway.

There are two known forms of cyclooxygenase, COX-1 and COX-2, which are encoded by two genes (Xie et al. 1991; O'Banion et al. 1992). COX-1 is constitutively expressed by many tissues and provides a homeostatic level of prostaglandins for the body and specific organs, such as the stomach and kidneys (Vane et al. 1998). In contrast, COX-2 is inductively expressed in vitro by a diverse array of cell stimuli such as exposure to lipopolysaccharide (O'Sullivan et al. 1992a; O'Sullivan et al. 1992b), certain cytokines and growth factors (O'Banion et al. 1992; Wadleigh and Herschman 1999), or mechanical stress (Topper et al. 1996; Klein-Nulend et al. 1997). COX-2 expression can be stimulated in vivo by wounding and inflammation (Masferrer et al. 1994; Shigeta et al. 1998; Muscaráet al. 2000).

Inhibiting the cyclooxygenase activity of COX-1 and COX-2 can reduce prostaglandin synthesis by preventing the conversion of arachidonic acid into $PGG_2$, the precursor of $PGH_2$. This is commonly done to reduce inflammation and pain with aspirin and non-steroidal anti-inflammatory drugs (NSAIDs), such as indomethacin. Most NSAIDs inhibit the cyclooxygenase activity of COX-1 and COX-2 with near equal potency, which often leads to detrimental gastro-intestinal or kidney side effects (Raskin 1999; Whelton 1999). Use of COX-2-selective NSAIDs has become very popular since these drugs, such as celecoxib (Celebrex) and rofecoxib (Vioxx) preferentially inhibit the cyclooxygenase activity of COX-2 with selectivity relative to COX-1 of approximately 8-fold for celecoxib and 35-fold for rofecoxib (Riendeau et al. 2001).

Prostaglandins are produced during fracture healing. Prostaglandin levels in and around the healing callus of rabbit tibia that had been severed by osteotomy showed that PGE and PGF levels were elevated between 1 and 14 and 7 and 14 days post-osteotomy, respectively (Dekel et al. 1981). No survey of the temporal pattern or variety of prostaglandins produced during fracture healing has been reported for other rodents or man. Non-specific NSAIDs have been shown to delay but not stop fracture healing in experimental animal models (Rø et al. 1976; Allen et al. 1980; Altman et al. 1995). In addition, non-specific NSAIDs have been shown to reduce the incidence and severity of heterotopic (abnormal or deviating from the natural position) bone formation in humans following certain fractures or orthopaedic surgical procedures (Pritchett 1995; Moore et al. 1998). These observation suggest that prostaglandins are necessary for bone formation but given the limitations of non-specific NSAID use, it is unknown whether prostaglandins produced by COX-1, COX-2 or both enzymes are essential for fracture healing.

SUMMARY OF THE INVENTION

The present invention relates to compositions and methods for use in wound healing and for use in enhancing fracture healing, bone formation and wound healing. The present invention further provides for methods for treating diseases related to bones, including osteoporosis, osteogenesis imperfecta and fibrodysplasia ossificans progressiva.

One embodiment of the present invention involves a vector for use in wound healing comprising a promoter linked to a cyclooxygenase expression cassette. In a further embodiment, the vectors of this invention may be used in gene therapy approaches to enhance wound healing. The wound conditions of this invention can include, bone fractures and skin lesions. The methods of this invention are particularly useful for wound healing in the elderly, patients with osteoporosis and OI, and patients that suffer from delayed wound healing.

In another embodiment, cyclooxgenase proteins, including COX-1, COX-2 or a combination of the two, are formulated as pharmaceutical compositions for use in wound healing. In a further embodiment of the invention, the pharmaceutical compositions are combined with a carrier for applications in wound healing.

Another embodiment of the invention provides for the use of the vectors of this invention in gene therapy approaches and/or the pharmaceutical compositions to treat osteoporosis, OI and other related brittle bone conditions. In a further embodiment, the vectors and compositions are used therapeutically to counteract conditions associated with osteoporosis, OI and brittle bones conditions. In a further embodiment, the vectors and compositions are used for wound healing and/or to enhance wound healing in patients with osteoporosis, OI or brittle bone conditions.

In another embodiment of the invention, COX-2 selective NSAIDs are used in the treatment of heterotopic ossification conditions. Such conditions can include fibrodysplasia ossificans progressiva. In addition, heterotopic ossification can occur following hip replacement procedures and after acetabular fractures. COX-2 selective NSAIDs can be used to treat heterotopic ossification under these circumstances as well.

BRIEF DESCRIPTION OF THE DRAWINGS

FIG. 1. Radiographic Analysis of Fracture Healing in NSAID Treated Rats

High resolution radiographs were made immediately post-fracture and then every week till the endpoint of the experiment (8 weeks) using a Hewlett-Packard Faxitron. Shown are radiographs of the fractured right femurs from the same rats taken at 2 (top), 4 (middle), and 8 weeks (bottom) post-fracture (dorsal-ventral view). As indicated, panels A-D shows radiographs from a no drug rat, an indomethacin treated rat, a celecoxib treated rat, and a rofecoxib treated rat, respectively. Note that the fracture is still clearly evident in the 8-week post-fracture radiographs of the celecoxib and rofecoxib treated rats.

FIG. 2. COX-2-Selective NSAIDs Alter the Mechanical Properties of Fractured Femurs Mechanical testing data was obtained or derived as described in the Experimental Procedures. The data for each fractured femur was normalized as a percentage of the value obtained from that animal's contralateral, unfractured femur, except for shear modulus panel D). Shown are the mean normalized values at each time point and for each treatment group or the mean shear modulus values in panel D. The error bars represent standard errors of the mean. Pairwise t-test were made between the no drug and experimental treatments within a time point. Statistical significance differences ($P<0.05$) are noted with asterisks.

FIG. 3. COX-2-Selective NSAIDs Disrupt Endochondral Ossification During Fracture Healing Shown are fracture calluses from no drug, indomethacin, celecoxib, and rofecoxib treated rats at 2, 3, and 4 weeks post-fracture as indicated. The specimens were embedded in polymethylmethacrylate (PMMA), sectioned, and stained with van Gieson's picrofuchsin and Stevenel's blue so that bone is red, calcified cartilage is orange to red, cartilage is deep blue to purple, and fibrous tissue and muscle is pale blue. Each section is oriented with the cortical bone on the bottom, fracture callus on top, and fracture site in the middle. Note the abnormal cartilage morphology in the calluses of the NSAID treated rats (panels D, G, and J) and the lack of cartilage in the celecoxib (panels H and I) and rofecoxib treated (panels K and L) rats at 3 and 4 weeks post-fracture.

FIG. 4. Abnormal Bone Resorption during Fracture Healing in COX-2-Selective NSAID Treated Animals Shown are fracture calluses from rofecoxib treated rats at 3 (panels A and B) and 4 weeks (panel C) post-fracture. The orientation of panels A and B are the same with external callus on top and fracture site to the immediate left of the panel. In panel C, the external callus is to the left and the fracture site is at the immediate bottom of the panel. The specimens were embedded in PMMA, sectioned, and stained with van Gieson's picrofuchsin and Stevenel's blue so that bone is red, calcified cartilage is orange to red, cartilage is deep blue to purple, and other cell types are shades of blue. Original photographic magnification is indicated. CB: cortical bone; WB: woven bone; CC: calcified cartilage; Ca: cartilage; F: fracture site; ab: air bubble; M: area of magnification shown in panel B; and Oc: osteoclasts. The NSAID treated rats often developed areas of high bone resorption at the cortical bone, fracture site, external callus junction (M) as seen in panel A. The air bubble (ab) seen in panel A is an artifact of the PMMA embedding. At higher magnification, osteoclasts (Oc) can be seen lining the cortical bone surface of area M in the 3 week fracture callus as denoted by the arrows. Shown in panel C is an identical area of a 4 week post-fracture callus as shown in panel B. The extent and area of bone resorption appears to be greater at 4 weeks post-fracture and also often encompassed all surfaces of the cortical bone at the fracture site. Similar bone resorption patterns were seen in celecoxib treated rats and to a lesser extent in the indomethacin treated rats.

FIG. 5. Experimental Complications Associated with NSAID Treatment during Fracture Healing Complications that necessitated the pre-mature euthanization or resulted in the pre-mature death of a rat during the course of these experiments were compiled and used to determine the effects of NSAID treatment on anesthetic death, infection, and pin slippage. Experimental treatment group values were compared to the no drug values using a $\chi^2$ analysis. Significant differences are noted with an asterisk ($P<0.01$). As can be seen, pin slippage was by far the most common complication and was significantly different for each treatment group relative to the no drug rats with P-values of less than $1E^{-4}$, $1E^{-7}$, and $1E^{-24}$ for the indomethacin, celecoxib, and rofecoxib treated rats respectively. The rofecoxib treated rats were also found to have a statistically significant higher infection rate as compared to the no drug rats ($P<0.0001$). Death from anesthesia was not different between groups.

FIG. 6. Cox2 but not Cox1 is Essential for Normal Bone Fracture Healing

The right femora of $Cox1^{-/-}$ and $Cox2^{-/-}$ mice were fractured and examined radiographically and histologically at 2 weeks post-fracture. Panels A and D. Radiographs of fractured femurs from a $Cox1^{-/-}$ and a $Cox2^{-/-}$ mouse, respectively. Note the lack of mineralized tissue (X-ray dense) in the fracture callus region of the $Cox2^{-/-}$ mouse. Panels B and C. Sagital section through the fractured femur of a $Cox1^{-/-}$ stained with Masson's trichrome stain (cell nuclei=purple; muscle and cytoplasm=red; collagen and bone=blue). Panels E and F. Sagital section through the fractured femur of a $Cox2^{-/-}$ stained with Masson's trichrome stain. Note the presence of chondrocytes within the $Cox2^{-/-}$ callus but the lack of endochondral ossification relative to the $Cox1^{-/-}$ mouse fracture callus. Original photographic magnification is indicated. The $Cox2^{-/-}$ mouse fracture callus specimens are shown at higher magnification because the callus was smaller.

B: bone; C: chondrocytes and cartilage; E: area of endochondral ossification; M: area of intramembraneous bone formation; F: fracture site.

DETAILED DESCRIPTION OF THE INVENTION

The present invention involves methods for enhancing wound healing and treating conditions of the bone with the use of cyclooxygenase (COX). COX is an enzyme that converts arachidonic acid into prostaglandin $H_2$ ($PGH_2$). $PGH_2$ is then converted into specific prostaglandins, which affect bone metabolism and formation. There are two forms of cyclooxygenase, COX-1 and COX-2. COX-1 is constitutively expressed, while COX-2 is inductively expressed by various stimuli. Examples of such stimuli are wounding and inflammation. The subsequent expression of COX-2 in response to these stimuli results in the production of pro-inflammatory prostaglandins. The pain and inflammation associated with a wound are commonly treated with non-steroidal anti-inflammatory drugs (NSAIDs). Most NSAIDs inhibit the cyclooxygenase activity of both COX-1 and COX-2. However, due to the inhibition of COX-1 activity, gastro-intestinal and kidney side effects result from NSAIDs use. COX-2 selective NSAIDs have also been developed which preferentially inhibit COX-2 activity relative to COX-1 activity and thereby avoid the side effects associated with non-specific NSAIDs.

In addition to its inflammatory function, one aspect of the invention relates to the necessity of COX-2 activity in wound healing. As described in more detail below, COX-2 is essential for normal wound healing. In another aspect of the invention, treatment systems and methods employ COX-2 to enhance wound healing.

In a preferred embodiment of the invention, gene therapy techniques are employed to increase cyclooxygenase activity at the site of the wound to enhance wound healing. Gene therapy techniques allow an absent or faulty gene to be replaced with a working gene. They also allow for the delivery and controlled expression of therapeutic gene products. One embodiment of the invention provides for a vector containing a cyclooxygenase expression cassette. In a further embodiment, the vector containing the cyclooxygenase expression cassette is delivered to the wound using gene therapy techniques. The gene therapy techniques may use adenoviral vectors, adeno-associated viral vectors, recombination-defective retrovirus vectors or DNA vectors to deliver the cyclooxygenase expression cassette to the wound.

The vectors of this invention may be used to increase cyclooxygenase levels at the site of the wound and thereby enhance would healing. For example, these vectors may be used to enhance wound healing following bone fractures or orthopaedic procedures. The vectors may also be of particular use to the elderly and other patient groups that have delayed bone healing, including smokers, diabetics, and steroid users. In addition, the vectors may be used in the treatment of osteoporosis and osteogenesis imperfecta using gene therapy techniques for gene replacement and to enhance healing for wounds resulting from these diseases.

One aspect of the invention involves a vector that contains a cyclooxygenase expression cassette that encodes a cyclooxygenase gene product. The vector includes all necessary sequences for the expression of the cyclooxygenase expression cassette and any sequences that may be included to control the expression of the cassette. These sequences may include, but are not limited to, a promoter or initiation sequence, an enhancer sequence, termination sequence, RNA processing signals, and/or a polyadenylation signal sequence.

The term "vector" refers to a nucleic acid construct that encodes for a particular gene product. The vectors of the present invention are preferably adenoviral, adeno-associated viral, recombination-defective retrovirus, plasmid or DNA vectors.

The term "cyclooxygenase expression cassette" refers to nucleic acid which codes for the cyclooxygenase enzyme, preferably COX-1 or COX-2. The expression cassette is positioned within the vector such that it can be transcribed into RNA and translated into the cyclooxygenase protein product. Table 3 provides for the human cDNA sequences for COX-1 (SEQ. ID. NO. 1) and COX-2 (SEQ.ID. NO. 2).

The term "necessary sequences for the expression of cyclooxygenase" refers to sequences necessary to ensure the transcription and translation of the expression cassette. The term "promoter" refers to a DNA sequence that is bound by RNA polymerase and is required to initiate transcription of a gene. There are a number of promoters that are known in the art, including those that can enhance or control expression of the gene or expression cassette. For example, cytomegalovirus promoter may be fused to the cyclooxygenase expression cassette to obtain constitutive expression of cassette or a COX-2 promoter may be linked to a cyclooxygenase cDNA to allow for expression of cyclooxygenase in a more normal fashion. For example, a COX-2 promoter may be linked to a COX-1 cDNA. This may allow a patient to remain on COX-2 selective NSAIDs but still have the ability to heal. In another aspect of the invention, the promoter may be induced in response to inflammation. Preferably, the inducible promoter employs the use of inflammatory gene promoters such as the interleukins, in particular, the IL-6 promoter, or the complement system gene promoters. Other inflammatory gene promoters include promoters for TNF-α, or the NF-κB response element.

In another aspect of the invention, the vectors are delivered directly to the location of the wound by injection or direct application in order to enhance wound healing. The vectors of this invention may also be administered by electroporation or delivered as an aerosol. The vectors may be administered or delivered in saline solutions, encapsulated in liposomes, in polymer solutions, in gels or lyophilized. In an alternative aspect, targeted transfection may be used to deliver the vectors in vivo. The term "wound" refers to a bone fracture, the site of a surgical orthopaedic procedure, or a skin lesion. In another aspect of the invention, the vectors may be delivered ex vivo, wherein a patient's cells are transfected ex vivo with the vectors of this invention and the transfected cells are then returned to the patient.

A further aspect of this invention provides for pharmaceutical compositions and methods of their use in wound healing. These pharmaceutical compositions include cyclooxgenase protein formulations and/or pharmaceutically acceptable carriers. The cyclooxgenase protein formulations comprise COX-1 protein, COX-2 protein or a combination of the two that are formulated such that the proteins remain stable, retain their function, including their enzymatic activity, and are physiologically acceptable. The human amino acid sequences for COX-1 (SEQ. ID. NO. 3) and COX-2 (SEQ. ID. NO. 4) proteins are provided in Table 3. There are a variety of pharmaceutically acceptable carriers that are known in the art, including, but not limited to, saline, liposomes, gels and polymers. The formulation and/or carrier may also be lyophilized for aerosol delivery. In a further embodiment of the invention, these pharmaceutical compositions are administered topically, orally, intravenously, nasally or via inhalation, or locally for use in wound healing. Preferably, these composition are administered to enhance wound healing.

In another aspect of the invention, methods of enhancing wound healing in the elderly are provided. COX-2 gene expression is reduced with age as are wound healing and bone formation. In one embodiment, vectors containing cyclooxygenase expression cassettes are administered to elderly to enhance would healing by increasing COX-2 expression during wound healing. A further aspect of this invention provides for methods for enhancing wound healing in patient groups that have delayed wound healing by delivering the vectors of this invention to these patients during wound healing.

In another embodiment of the invention, the vectors of this invention are used to enhance wound healing in patients suffering from osteoporosis or OI by employing gene therapy techniques to deliver cyclooxygenase expression cassettes to the wound to enhance healing.

In another aspect of the invention, a method for treating pathological heterotopic ossification conditions is provided. Pathological heterotopic ossification conditions are diseases characterized by abnormal bone formation at locations of inflammation. An example of a pathological heterotopic ossification condition is fibrodysplasia ossificans progressiva (FOP). In one embodiment of the invention, COX-2 selective NSAIDs are administered to locations of inflammation that lack a wound. The COX-2 selective NSAIDs inhibit COX-2 activity thereby preventing abnormal bone formation.

Our experimental approach was to assess fracture healing using a standard rat closed femur fracture model in which COX-2 function was inhibited in vivo with the COX-2-selective NSAIDs, celecoxib and rofecoxib. The results were striking in that femur fracture healing in rats treated with celecoxib or rofecoxib was dramatically impaired. These observations were confirmed by examining fracture healing in Cox1 and Cox2 null mice. Histological observations indicated that the defect in fracture healing caused by the COX-2-selective NSAIDs or by lack of Cox2 occurred in the endochondral ossification pathway.

Using a standard rat closed femur fracture model, we have demonstrated that COX-2-selective NSAID treatment can stop normal fracture healing and induce the formation of mal-unions and non-unions. Non-unions refer to fractures that show no visible sign of healing. Mal-unions refer to bones that do not heal properly and result in misalignment of bones. These observations are in grim contrast to those observations we, and others have obtained by treating rats with non-selective NSAIDs such as indomethacin when it was observed that fracture healing was delayed but not prevented (Rø et al. 1976; Rø et al. 1978). Our observations suggest that COX-2 has an essential function during normal fracture healing and that COX-2-selective NSAID inhibition of prostaglandin synthesis stops normal fracture healing. This also suggests that the inflammatory phase is critical for normal fracture healing.

Consistent with the effects of COX-2-selective NSAIDs on rat femur fracture healing, mice homozygous for a targeted mutation in Cox2, but not Cox1, also showed inhibited fracture healing (FIG. 6). The cDNA sequences (SEQ. ID. NO. 5 for COX-1 and SEQ. ID. NO. 6 for COX-2) and corresponding amino acid sequences (SEQ. ID. NO. 7 for COX-1 and SEQ. ID. NO. 8 for COX -2) for mouse COX-1 and COX-2 gene and protein are provided in Table 4. This excludes the possibility that any additional inhibitory activity against other cellular processes or proteins by celecoxib or rofecoxib (Jones et al. 1999; Hsu et al. 2000: Rossi et al. 2000) is primarily responsible for negatively affecting fracture healing.

The amount of rofecoxib used to treat the rats (3 mg/kg) in this study was approximately 4 times the nominal, maximum human daily dose of 50 mg (0.7 mg/kg) that is used to manage acute pain. In contrast, the celecoxib dose used to treat rats in this study was in the recommended dose range for humans. The rats received 280 mg/70 kg body weight of celecoxib once per day whereas the recommended human maximum daily dose of celecoxib is 200 mg twice a day. Additionally, the rats in this study received daily doses of each drug till the endpoint of the experiment, which is unlike common clinical scenarios when COX-2-selective NSAIDs are used to acutely manage pain, inflammation, and swelling following a fracture. In contrast, arthritis patients, in particular, do use COX-2-selective NSAIDs on a daily basis for extended periods. Based simply upon animal body weight and drug dose, and without accounting for pharmacokinetic variables, the indomethacin dose used (1 mg/kg) would be predicted to inhibit most COX-1 activity but to only partially inhibit COX-2 activity; the celecoxib dose used should inhibit most if not all COX-2 activity and possibly inhibit some COX-1 activity; and the rofecoxib dose used should completely inhibit COX-2 activity but not affect COX-1 (Warner et al. 1999). The estimated plasma half-lives for celecoxib and rofecoxib in male rats following a single drug dose are approximately 4 and 5 hours respectively (Halpin et al. 2000; Paulson et al. 2000). In humans, however, the estimated elimination half-life for celecoxib is 11 hours (Davies et al. 2000) and the plasma half-life for rofecoxib is approximately 10-17 hours depending upon drug dose (Depré et al. 2000). Unfortunately, these data were unknown to us when this study was initiated and consequently our rat drug dosing regime may actually be an under representation of the COX-2 inhibition level over a 24 hour cycle as that for humans receiving similar drug doses. Additionally, celecoxib and rofecoxib may have different inhibitory concentrations for rat versus human COX-2. Despite the pharmacokinetic variations between rats and humans receiving COX-2-selective NSAIDs, our data clearly indicate that these drugs have a dramatic negative effect on fracture healing in mammals, and thus caution in the use of these COX-2-selective NSAIDs in humans is warranted.

The fractured femurs of the celecoxib treated rats had increased mechanical properties and healed as mal-unions, rather than non-unions, in approximately 50% of the rats tested (Tables 1 and 2). Had the experimental endpoint been extended, some of the celecoxib treated rats may have gone on to heal their femur fractures. However, the delay in any such healing among the celecoxib treated rats would have been significantly longer than in no drug or indomethacin treated rats.

After mechanically testing the celecoxib and rofecoxib treated fractured femurs, we observed that the fracture callus had a shell-like morphology. The periphery of the fracture callus was bone that sometimes partly bridged the fracture gap and thus formed a mal-union in the celecoxib treated rats. However, little or no bone was present between the peripheral bone of the callus and the original femoral cortical bone ends. Often this space appeared to be filled with fatty marrow. Also strikingly apparent was the lack of new bone or primary bone healing at the cortical bone ends.

The indomethacin dose used in this study (1 mg/kg) was previously shown to delay fracture healing in rats and was used principally as a positive control (Altman et al. 1995). Increasing indomethacin doses to levels that which would completely inhibit COX-2 (and COX-1 activity) causes a steep increase in rat mortality from gastrointestinal bleeding (Allen et al. 1980; Wallace et al. 1998). Consequently, it would be difficult to directly compare the effects of COX-2-selective and traditional NSAIDs on fracture healing based solely upon COX-2 inhibition levels. An alternative approach would be to measure prostaglandin levels within and around the fracture callus during healing in control and drug treated rats and to then correlate those observations with different healing parameters.

The abnormal osteoclastic response observed at the fracture site in the NSAID treated rats is counter to experimental observations in which prostaglandins stimulate bone resorption (Klein and Raisz 1970) and COX-2 function promotes osteoclast formation (Okada et al. 2000). Lack of prostaglandins in the fracture callus could induce osteoclastic activity through an undescribed mechanism, or perhaps through an indirect mechanism such as increased mechanical instability at the fracture site. An additional possibility is that the amount and/or repertoire of prostaglandins produced at the fracture site in the NSAID treated rats is competent for inducing osteoclastic activity but insufficient for osteogenesis to proceed normally. The second possibility is favored since the relative short half-life of celecoxib and rofecoxib in rats should produce daily periods in which COX-2-dependent prostaglandin synthesis could occur and because a similar osteoclastic response was not observed in the $Cox2^{-/-}$ mouse fracture callus (FIG. 6). In addition, this large osteoclastic activity may be the causative factor involved in fracture destabilization by pin slippage, which was the major morbidity complicating these experiments (FIG. 5).

Chondrocyte differentiation and persistence in the fracture callus appears to be altered by COX-2-selective NSAID treatment and by lack of Cox2 (FIG. 6). Cartilage that is evident in the 2-week fracture calluses of COX-2-selective NSAID treated rats either disappears or is dramatically reduced in the 3 and 4-week fracture calluses (FIG. 3). In control rats, the fracture has bridged or is almost bridged by 4 weeks post-fracture as the cartilage present at early times had undergone normal endochondral ossification and is no longer evident. In contrast, cartilage within the indomethacin treated fracture callus does persist at 4 weeks post-fracture indicating a reduced rate of endochondral ossification. These observations suggest that the chondrocytes within the COX-2-selective NSAID treated rats deteriorated without forming a cartilage matrix in which endochondral ossification could occur. This phenomenon then leads to the development of fracture non-unions and mal-unions. Similar histological observations were seen in the $Cox2^{-/-}$ mouse fracture where chondrocytes present in the callus failed to form a mineralized matrix (FIG. 6). In support of this hypothesis, teratocarcinoma chondrocytes developed from $Cox2^{-/-}$ embryonic stem cells were found to be deteriorating, hypotrophic, and undergoing apoptosis (Zhang et al. 2000). Additionally, the $Cox2^{-/-}$ mouse fracture callus was much smaller than that from the $Cox1^{-/-}$ mouse suggesting that mesenchymal cell proliferation and migration into the $Cox2^{-/-}$ mouse fracture site is reduced or that the mesenchymal cells proportionately differentiate into fewer chondrocytes. Thus, COX-2 function is essential for normal progression of endochondral ossification during fracture healing.

There are several steps during endochondral ossification at which COX-2 could exert an essential regulatory function. Endochondral ossification is a complicated process that begins when chondrocytes mature to produce a cartilage matrix. Eventually the chondrocytes become hypertrophic and undergo apoptosis as the cartilage matrix matures and becomes calcified. Osteoclasts partially resorb the calcified cartilage with concurrent angiogenesis at the site of endochondral ossification. Osteoblasts proliferate and differentiate on the calcified cartilage and begin forming new bone. Remodeling of the new bone subsequently occurs to increase the mechanical properties of the bone and restore its normal architecture. Prostaglandins produced by COX-2 could be used to enhance osteoblast proliferation and differentiation (Kawaguchi et al. 1995). Prostaglandins may also be necessary to promote terminal differentiation of chondrocytes and formation of the cartilage matrix. Such an effect on chondrocytes could occur through a direct effect on differentiation or indirectly by preventing pre-mature apoptosis since inhibition of COX-2 function by COX-2-selective NSAIDs has been shown to induce apoptosis in cancer cell lines (Hsu et al. 2000). The potential effects of prostaglandins on osteoblasts and chondrocytes during endochondral ossification are not mutually exclusive. An additional possibility is that COX-2 dependent signaling occurs between osteoblasts and chondrocytes to initiate and maintain endochondral ossification. Prostaglandins are also known to promote osteoclast activity, which may be essential for the normal endochondral ossification process. However, our histological observations indicate an exuberant osteoclast response at the fracture site in the NSAID treated rats thus we do not favor this potential mechanism. Angiogenesis is also inhibited by COX-2-selective NSAIDs, at least in certain experimental models (Jones et al. 1999), and we failed to detect neovascularization of the $Cox2^{-/-}$ mouse fracture callus. Thus an additional possibility is that lack of angiogenesis precludes proper delivery of osteoclasts and osteoblasts to the cartilage matrix interface for continued endochondral ossification.

Our observations suggest that COX-2-selective NSAIDs may be effective in reducing or preventing pathological heterotopic ossification. One particular genetic disease for which COX-2-selective NSAIDs may be efficacious is fibrodysplasia ossificans progressiva (FOP)(Cohen et al. 1993). Children afflicted with FOP develop debilitating heterotopic bone through an endochondral ossification pathway that appears to initiate at sites of inflammation (Kaplan et al. 1993). Thus the COX-2-selective NSAIDs may be useful in reducing inflammation and stopping endochondral ossification at presumptive heterotopic ossification sites in children with FOP.

To determine if COX-2 functions in fracture healing, rats were treated with COX-2-selective non-steroidal anti-inflammatory drugs (NSAIDs) to stop COX-2-dependent prostaglandin production. Radiographic, histological, and mechanical testing demonstrated that fracture healing failed in rats treated with COX-2 selective NSAIDs. Normal fracture healing also failed in mice homozygous for a null mutation in the COX-2 gene. These results demonstrate that COX-2 activity is necessary for normal fracture healing and confirms that the effects of COX-2-selective NSAIDs on fracture healing is due to inhibition of COX-2 activity and not from a drug side effect. Furthermore, histological observations suggest that COX-2 is required for normal endochondral ossification during fracture healing. Since mice lacking Cox2 form normal skeletons, our observations indicate that fetal bone development and fracture healing are different and that COX-2 function is specifically essential for fracture healing.

Experimental Procedures

Animals, Drug Dosage, and Administration

A total of 253 male Sprague-Dawley rats (584±62g) were fed a standard diet and kept caged separately in a constant temperature and humidity environment. All rats were 6-9 months old at the beginning of the experiment. Drugs were administered daily by gavage beginning two days prior to fracture. Animals were randomly selected for each treatment group. The rats were gavaged with aqueous suspensions of indomethacin (1 mg/kg), celecoxib (4 mg/kg), or rofecoxib (3 mg/kg). No drug (control) rats were not initially gavaged but later rats were gavaged with water and no difference was noted between the no drug rats that had been gavaged and those that had not. No statistically significant differences were found in animal weight changes during the experiments.

Retired breeder female $Cox1^{-/-}$ (B6;129P2-Ptgs1$^{tm1}$) and $Cox2^{-/-}$ (B6;129P2-Ptgs2$^{tm1}$) mice were obtained from Taconic Farms. Closed femur fracture production was done using a method similar to that described below.

Closed Femur Fracture Production

The rats were anesthetized by intraperitoneal injection of ketamine (40 mg/kg) and xylazine (5 mg/kg). Under aseptic conditions, a medial parapatellar incision (0.4-0.5 cm) was made in the right hindlimb and the patella was dislocated laterally. The medullary canal was entered through the intercondylar notch and reamed with an 18-gauge needle. A 1.1 mm stainless steel pin (Small Parts Inc., Miami Lakes, Fla.) was then inserted into the canal and secured in the proximal part of the greater trochanter by tamping. The distal portion of the pin was then cut flush with the femoral condyles and the patella dislocation was reduced. The soft tissue and skin were closed with 4-0 vicryl sutures. After closing, the diaphysis of the pinned femur was fractured by means of a three-point bending device as described by Bonnarens and Einhorn (Bonnarens and Einhorn 1984).

Radiography

Radiographs were made post-fracture to confirm the position and quality of each fracture and at sacrifice to determine the degree of healing. In addition several rats were selected randomly to produce serial radiographs (at least 2 rats per treatment group). Radiographs were made of these rats weekly under anesthesia until the experimental endpoint (8 weeks). Radiographs of mice were also made under anesthesia. All radiographs were made using a 43805N Faxitron (Hewlett-Packard, McMinnville, Oreg.) and Kodak MinR-2000 mammography film.

Mechanical Testing

Animals within each treatment group were sacrificed at 4, 6, and 8 weeks post-fracture by $CO_2$ asphyxiation. Animals with oblique, comminuted, or infected fractures were not used for mechanical testing. Both femora were removed and cleaned of all soft tissue leaving the fracture callus undisturbed and then immediately processed for mechanical testing. The samples were wrapped in saline soaked gauze to prevent dehydration between steps. Measurements of the femora were taken using digital calipers to determine femur length and external callus dimensions. The intramedullary pin was removed from the fractured femur and a 1 mm-diameter stainless steel pin (~0.8 cm length) was inserted at the proximal and distal end perpendicular to the long axis of the bone to prevent slipping in the potting material. The intact femur was also pinned as described above. The femoral ends were potted in 1-inch hexnuts using a low melt temperature metal (Wood's metal, Alfa Aesar, Ward Mill, Mass.). Once potted, the gage length (L) of each femur was measured. Torsional testing was conducted using a servohydraulic testing machine (MTS, Eden, Praire, Minn.) with a 20 Nm reaction torque cell (Interface, Scottsdale, Ariz.). The testing was carried out to failure at a rate of 2°/sec and a data recording rate of 20 Hz. Both the fractured and intact femora were tested in internal rotation in proper anatomic orientation. The peak torque and angle at failure were calculated from the load-deformation curves. Internal fracture callus dimensions were measured after mechanical testing. From the callus dimensions, the polar moment of inertia (J) was calculated based upon a hollow ellipse model (Bell et al. 1941; Engesaeter et al. 1978). The equations used to derive torsional rigidity, shear stress, shear modulus, and J were as follows (Popov 1968): (1) Torsional Rigidity: $(T_{max} \cdot L)/\phi$ where $T_{max}$ is the peak torque value in Nmm, L is the gage length in mm, and $\sigma$ is the angle at failure in radians. (2) Shear Stress: $(T_{max} \cdot R_{max})/J$ where $R_{max}$ is the largest radial dimension of the fracture callus in mm ($a_o$) and J is the polar moment of inertia. (3) Shear Modulus (G): $(T_{max} \cdot L)/J$. (4) Polar Moment of Inertia (J): $[\pi(ab^3 + a^3b - (a-t)(b-t)^3 - (a-t)^3(b-t)]/4$ where a is $[a_i + [(a_o - a_i)/2]$; b is $[b_i + [(b_o - b_i)/2]$; t is the average bone thickness at the site of failure and is calculated as $[(a_o - a_i) + (b_o - b_i)]/2$ where $a_o$ is the callus maximum outside radius, $a_i$ is the maximum interior radius, $b_o$ is the least outside radius, and $b_i$ is the least interior radius in mm. Only torsional testing data for which the fractured and control femur tested without incident were used.

Histology

Rats were sacrificed at 2, 3, 4, 6, and 8 weeks post-fracture by $CO_2$ asphyxiation. Both femora were resected and the stainless steel pin was removed from the medullary canal. The harvested femora were fixed in 10% buffered formalin and embedded in polymethylmethacrylate following standard histological techniques for calcified tissue. The samples were sectioned sagitally through the fracture callus using an Isomet diamond saw (Buehler Ltd., Lake Bluff, Ill.), mounted on plexiglass slides, and polished to a thickness of 100 μm. The slides were then stained with van Gieson's picrofuchsin and Stevenel's blue in order to identify new bone growth and cartilage formation (Maniatopoulos et al. 1986). Mice femora were fixed, decalcified, paraffin embedded, sectioned, and stained with Masson's trichrome stain. The samples were viewed and photomicrographs were taken using an Olympus BH2-RFCA microscope or an Olympus SZ40 microscope.

Treatment with COX-2-selective NSAIDs Leads to Fracture Non-Unions and Mal-Unions Femur fracture healing was followed by serial radiographic analysis of rats treated with celecoxib, rofecoxib, indomethacin, or gavaged daily with water (no drugs group). Radiographs were made immediately following fracture production and then every week till the end point of the experiments (8 weeks post-fracture). Representative results are shown in FIG. 1.

We found that femur fracture healing proceeded normally in the no drug rats as expected. At 1 week post-fracture, formation of the hard callus could be detected radiographically but was more evident at 2 weeks (FIG. 1A). By 4 weeks post-fracture, calcification of the soft callus was clearly evident indicating that endochondral ossification had occurred. Additionally, by 4 weeks post-fracture, the new bone formed during fracture repair had almost bridged the fracture gap. Bridging of the fracture and remodeling of the fracture callus were evident at 6 weeks post-fracture. Continued remodeling of the callus as well as remodeling of the original femoral cortical bone at the fracture site is clearly evident by 8 weeks post-fracture. These radiographic observations are typical of normal fracture healing.

Indomethacin treatment appeared to delay but not prevent fracture healing consistent with previous reports (Rø et al. 1976; Allen et al. 1980; Altman et al. 1995). By 2 weeks post-fracture, an X-ray dense hard callus is clearly evident in the indomethacin treated rats (FIG. 1B). However, bridging of the fracture gap did not appear to occur until 5-6 weeks post fracture as compared to approximately 4-5 weeks post-fracture in the untreated rats (compare FIGS. 1A and B). Bridging and remodeling were evident in the 8 week post-fracture radiographs of the indomethacin treated rats.

Celecoxib or rofecoxib treatment did not prevent formation of an X-ray dense hard callus as can be seen in the 2 and 4 week post-fracture radiographs (FIGS. 1C and D). However, the original fracture was still plainly evident in the celecoxib (FIG. 1C) and rofecoxib (FIG. 1D) treated rats even after 8 weeks. No rofecoxib treated rat was observed to have a normally bridged callus by radiography. However, non-unions, mal-unions, and unions of the fractured femurs were observed by radiography in the celecoxib treated rats. The mal-unions were typified by the radiograph seen in FIG. 1C in which one cortex of the fracture callus was bridged but in which the original cortical bone ends of the fractured femur had not joined and the fracture was still clearly evident.

In addition to the serial radiographs made for certain rats, all animals in this study were examined radiographically immediately post-fracture and when euthanized. A random, blinded sample of the 8-week post-fracture radiographs were independently examined by 7 observers and scored as a union (1 point), mal-union (0.5 points), or non-union (0 points). Control rats had an average score of 0.71. In contrast, the indomethacin, celecoxib and rofecoxib treated rats had average scores of 0.54, 0.49, and 0.32, respectively. Despite the known difficulties associated with judging fracture healing from radiographs (Nicholls et al. 1979; Panjabi et al. 1989), a statistical comparison between treatment groups showed that the no drug and rofecoxib groups were significantly different ($P<0.007$ using a Fisher's PLSD test at a 5% significance level).

These observations clearly indicate that rofecoxib treatment inhibits fracture healing in rats leading to non-unions. It would also appear that at least by radiographic examination, celecoxib treatment negatively affects fracture healing to an extent similar to, if not worse than, indomethacin treatment.

The Mechanical Properties of the Healing Femur Fracture Callus are Diminished by NSAID Treatment In conjunction with the radiographic analysis, torsional mechanical testing of fractured femurs was also performed. The fractured femur and contralateral control femur from rats at 4, 6, and 8 weeks post-fracture were tested to failure in torsion for each treatment group (no drugs, indomethacin, celecoxib, and rofecoxib). The data from these tests is summarized in FIG. 2 and Table 1. Peak torque is the maximum twisting force generated during torsional testing of the femur. Torsional rigidity is a measure of a structure's resistance to torque. Thus a bone with high torsional rigidity would fail after only a few degrees of rotation, but soft tissue would not reach its peak torque until after a large angular deflection. Maximum shear stress is a measure of the ultimate shearing force withstood by the femur prior to failure and is a function of the applied torque and polar moment of inertia, which is dictated by callus geometry. Shear modulus measures the elastic resistance to deformation by a shearing stress for a given material and is constant for a given material.

We found in the no drug rats that the normalized peak torque (101%) and torsional rigidity (88%) of the fractured femur was restored by 8-weeks post-fracture as compared to the contralateral control femurs from each animal (FIG. 2). However, the shear modulus (1.3 GPa) and normalized shear stress (48%) of the fractured femurs at 8 weeks post-fracture were still less than the contralateral control femurs (FIG. 2, Table 1). This is the expected result because during fracture healing, the ultimate mechanical integrity of the fractured bone, that is peak torque, is maintained at a high level by increasing bone diameter via the fracture callus. Since the mechanical properties of the initially soft tissue within the callus and later the newly formed bone are much weaker than the mechanical properties of mature cortical bone; shear stress and shear modulus were, as expected, less than the contralateral control femurs. As the newly formed bone within the fracture callus matures by remodeling, the mechanical properties of the fractured bone increase. This is evident in our results as increases in shear stress and shear modulus with time (FIG. 2). The high normalized torsional rigidity found for the fractured femurs in the no drug rats at 6 (89%) and 8 (88%) weeks post-fracture indicates that the fracture had been bridged by new bone as would be expected.

We also observed that all of the 6 and 8 week post-fracture no drug femurs and all the contralateral control femurs failed as predicted, mid-diaphyseal spiral fractures during the torsional mechanical testing.

Indomethacin treatment reduced the mechanical properties of the healing femur fractures at earlier time points (FIG. 2). However by 8 weeks post-fracture, the normalized peak torque, torsional rigidity, and shear stress values obtained from the indomethacin treated rats were not significantly different from the no drug rats. In contrast, at 6 weeks post-fracture, the normalized peak torque, torsional rigidity, and shear stress values (46, 34, and 15%, respectively) obtained from the indomethacin treated rats were less than the no drug rats at 6 weeks post-fracture (77, 89, and 36%, respectively). Pointedly, the significantly low torsional rigidity of the fractured femurs from the indomethacin treated rats at 6 weeks post-fracture indicates that the fracture had not been bridged by bone. Of the eight fractured femurs tested at 8 weeks post-fracture, 6 failed as unions, 1 failed as a mal-union, and 1 failed as a non-union (Table 2). These observations indicate that the non-selective NSAID, indomethacin, delays, but does not prevent fracture healing, which is consistent with previous studies and demonstrates the validity of our assay methods (Rø et al. 1976; Allen et al. 1980; Altman et al. 1995).

Rofecoxib treatment had a drastic effect on the mechanical properties of the fractured femurs. At 8 weeks post-fracture, for all values measured or derived, the mechanical properties of the fractured femurs from the rofecoxib treated rats were significantly less than the no drug rat fractured femurs (FIG. 2, Table 1). At 8 weeks post-fracture, the fractured femurs of the rofecoxib treated rats had only obtained 50%, 31%, and 18% of peak torque, torsional rigidity, or maximum shear stress of the contralateral unfractured femurs, respectively. The low torsional rigidity and shear modulus (0.5 GPa) values obtained from the fractured femurs of the rofecoxib treated rats are consistent with healing failure and the formation of non-unions. In addition, whereas all of the contralateral control femurs from the rofecoxib treated rats failed as mid-diaphyseal spiral fractures, 4 of the 5 fractured femurs at 8 weeks post-fracture failed as non-unions and the other failed as a malunion (Table 2). These observations demonstrate that, at the dose and treatment regime employed, the COX-2-selective NSAID rofecoxib stops fracture healing.

Unlike rofecoxib treatment, no significant differences were found in the mechanical properties of the healing fractured femurs from the celecoxib treated rats as compared to no drug rats. Despite the overall similarities in the mechanical values obtained between no drug rats and celecoxib treated rats, 3 of 6 fractured femurs from the celecoxib treated rats at 8 weeks post-fracture failed as non-unions during the mechanical testing procedure and the other 3 failed as mal-unions (Table 2).

The relatively low normalized torsional rigidity (50%) and shear stress (22%) found for fractured femurs from the celecoxib treated rats at 6 weeks post-fracture indicates that the fracture site had not been bridged with bone (FIG. 2). Even though not statistically different from the no drug rat fractured femurs, the data obtained from the celecoxib treated rat fractured femurs parallels closely the patterns obtained from the femurs of the indomethacin treated rats. Together these observations suggest that, at the celecoxib dose and treatment regime used, fracture healing is delayed and to a lesser extent than that found for the rofecoxib treatment regime, inhibited.

A $\chi^2$ analysis was performed on visual inspection data obtained from the 8 week post-fracture femurs following mechanical testing (Table 2). The fractured femurs were considered to have failed as (a) unions if a spiral fracture developed through the diaphysis of the femur, (b) non-unions if the femur failed completely along the original fracture site, and (c) mal-unions if some new bone bridging of the fracture site was evident but that the femur still failed primarily along the original fracture site. The data from the no drug, celecoxib, and rofecoxib treatment groups were compared to that from the indomethacin treatment group. Our analysis indicates that no statistical difference exists between the no drug and the indomethacin treatment groups but that the celecoxib and rofecoxib treatment groups are significantly different from the indomethacin treatment group. Again, these observations strongly indicate that inhibition of COX-2 dramatically inhibits fracture healing.

No significant differences in the mechanical properties of the contralateral femurs were found between treatment groups. This indicates that the experimental treatment regimes did not alter the intrinsic properties of the rat bone by enhanced bone resorption or deposition at least for the time frame examined.

COX-2-selective NSAID Treatment Alters Cartilage Formation During Fracture Healing The radiographic and torsional mechanic testing analyses of the COX-2-selective NSAID treated rats demonstrated that these drugs dramatically inhibit fracture healing. However, hard callus formation appeared not to be impaired in the COX-2-selective NSAID treated rats. This suggests that COX-2-selective NSAIDs impair fracture healing in the soft callus where endochondral ossification occurs. Since radiography cannot assess the early stages of endochondral ossification in the soft callus, we undertook a histological analysis of fracture healing in the drug treated rats.

At 2 weeks post-fracture, gross abnormalities were present in the histology of the healing femur fractures of the indomethacin, celecoxib, or rofecoxib treated rats as compared to an untreated control rat (FIG. 3). In all four experimental groups, significant periosteal intramembraneous ossification was evident at the fracture site as expected from our radiographic data. Endochondral ossification also appeared to be proceeding normally in the no drug rat specimens. In contrast, the histological specimens from the indomethacin and COX-2-selective NSAID treated rats had abnormally formed cartilage elements within the callus. The positional extent of new bone formed in the callus of the NSAID treated rats also appeared to be abnormal in that it did not fully extend to the ends of the fractured bone. In the no drug rats, new bone in the callus extends to the very ends of the cortical bone fracture site. This is not so in the NSAID treated rats where this region of the callus is generally occupied by cartilage.

NSAID treatment grossly altered fracture callus morphology at 3 and 4 weeks post-fracture (FIG. 3). Fracture healing proceeded normally in the no drug rats with near bridging of the callus apparent by 4 weeks post-fracture in concurrence with our radiographic data (FIG. 1). However, healing was clearly delayed in the NSAID treated rats. The fracture calluses of the indomethacin treated rats were not bridged at 4 weeks but still appeared to be undergoing endochondral ossification based upon the presence of cartilage within the soft callus at 3 and 4 weeks post-fracture. In contrast, little or no cartilage was evident in the fracture calluses of the celecoxib or rofecoxib treated rats at 3 and 4 weeks post-fracture indicating that endochondral ossification had ceased. Additionally massive resorption of the woven bone in the hard callus of the NSAID treated rats appeared to leave a shell-like callus on the ends of the fractured bone.

Celecoxib and rofecoxib treatment often caused a massive bone resorption event at the distal ends of the fracture bones leaving what appear to be indentations into the hard callus (FIG. 3 and 4). The magnitude of this bone resorption phase is indicated by the large number of osteoclasts that were found on the femur periosteal surface at the distal ends of the fractured bone near the apparent indentation (FIG. 4).

At 6 and 8 weeks post-fracture, the fractured femurs of the no drug rats appeared to be healing normally with active remodeling of the cortical bone ends and fracture callus. Fractured femurs from indomethacin treated rats also appeared to be healing at 6 and 8 weeks post-fracture with evident bridging and active remodeling. In contrast, no further healing was evident in the celecoxib or rofecoxib treated rat fractured femurs. The callus in the COX-2-selective NSAID treated rats was smaller at 6 and 8 weeks post-fracture but the fracture gap was still clearly evident and often filled with fibrous tissue. These observations are consistent with our radiographic and torsional mechanical testing data demonstrating that celecoxib and rofecoxib inhibit fracture healing.

Complications Associated with Use of COX-2-Selective NSAIDs

As can be seen in FIG. 5, pin slippage was a severe complication with as many as 30% of the rofecoxib treated rats having to be euthanized prior to the endpoint. Pin slippage is dislodgement of the intramedullary stainless steel rod used to stabilize the fracture and permit the rat to weight-bear on the fractured femur. Once fracture stability was lost, the rat was euthanized since the rat could no longer weight-bear on the femur and since the callus would be re-injured and thus alter healing. The etiology of the pin slippage is unknown. Animals with these complications were excluded. As such, final data may be skewed in favor of rats that had healed. Other complications included anesthesia death during weekly radiographs and infections that excluded specimens from further analysis. It was found using a $\chi^2$ analysis to compare each experimental group value to the no drug rat value that the pin slippage rate was significant for all NSAID treatment groups (P<0.0001) and that the infection rate for the rofecoxib treated rats was also significant (P<0.0001).

Normal Fracture Healing Fails in Cox2 Null Mice

Our data clearly demonstrate that COX-2-selective NSAIDs are detrimental to fracture healing. Unfortunately, these observations do not distinguish between a specific effect on COX-2 and a non-specific effect of the NSAIDs on fracture healing. Therefore to specifically address whether fracture healing requires Cox1 or Cox2 gene function, femur fracture healing was assessed in Cox1 and Cox2 knock-out mice (Langenbach et al. 1995; Morham et al. 1995). Using a modified method, closed femur fractures were produced in three female Cox1$^{-/-}$ (Cox1 knock-out) and three female Cox2$^{-/-}$ (Cox2 knock-out) mice. The animals were examined radiographically immediately post-fracture and then at 7, 10, 14, 21, 28, and 42 days post-fracture. Fracture healing appeared to proceed normally in the Cox1$^{-/-}$ mice relative to our previous observations in outbred and inbred strains of mice (Manigrasso and O'Connor, unpublished). In contrast, only a slight periosteal hard callus was detected in any of the Cox2$^{-/-}$ mice, which is indicative of healing failure. As can be seen in FIG. 6, the apparent difference in fracture callus size was most obvious at 2 weeks post-fracture when the Cox1$^{-/-}$ mice had formed a large fracture callus but little or no callus was evident in the Cox2$^{-/-}$ mice.

One mouse of each genotype was euthanized at 2 weeks post-fracture and the fractured femur examined histologically (FIG. 6). New bone and differentiating chondrocytes were abundant within the Cox1$^{-/-}$ callus indicating that COX-1 activity is not essential for fracture healing. In contrast, there was a plainly evident lack of new bone formation in the Cox2$^{-/-}$ fracture callus with only some apparent intramembraneous bone formation occurring at the edges of the callus (hard callus). Chondrocytes at different stages of differentiation were observed throughout the Cox2$^{-/-}$ soft fracture callus. However, the Cox2$^{-/-}$ chondrocytes failed to form a mineralized matrix as evident by the radiolucency and histological appearance of the soft callus. The amount of endochondral ossification at the hard callus-soft callus boundary appeared greatly reduced in the Cox2$^{-/-}$ specimen. In addition, neovascularization of the Cox2$^{-/-}$ fracture callus was not observed. These observations clearly indicate that normal fracture healing and endochondral ossification are stopped or dramatically reduced in the Cox2$^{-/-}$ mice and confirms our observations made in the COX-2-selective NSAID treated rats.

Our data indicate that COX-2 function is essential for fracture healing. In contrast, adult mice homozygous for targeted mutation of Cox2 appear to have normal skeletons. Together these observations demonstrate that fetal osteogenesis and fracture healing, though similar in many ways, are different and are probably initiated and maintained through different molecular mechanisms. Cox2 is the first gene to be identified that is specifically essential for fracture healing but not fetal osteogenesis. Targeted mutation of other mouse genes involved in prostaglandin synthesis and signaling should enable further analysis of the prostaglandin pathway(s) involved in fracture healing and skeletal biology in general.

One skilled in the art will readily appreciate that the present invention is well adapted to carry out the objects and obtain the ends and advantages mentioned as well as those inherent therein. The cyclooxygenase vectors along with the methods, procedures and treatments described herein are presently representative of preferred embodiments and are exemplary and not intended as limitations on the scope of the invention. Changes therein and other uses will occur to those skilled in the art which are encompassed within the spirit of the invention or defined by this scope with the claims.

It will be readily apparent to one skilled in the art that varying substitutions and modifications may be made to the invention disclosed herein within departing from the scope and spirit of the invention.

All patents and publications referenced herein are incorporated by reference to the same extent as if each individual publication was specifically and individually indicated to be incorporated by reference. The following references are likewise incorporated by reference in order to more fully describe the state of the art.

REFERENCES

Allen, H. L., A. Wase, and W. T. Bear. 1980. Indomethacin and aspirin: effect of nonsteroidal anti-inflammatory agents on the rate of fracture repair in the rat. *Acta. Orthop. Scand.* 51: 595-600.

Altman, R. D., L. L. Latta, R. Keer, K. Renfree, F. J. Hornicek, and K. Banovac. 1995. Effect of nonsteroidal antiinflammatory drugs on fracture healing a laboratory study in rats. *J. Orthop. Trauma* 9: 392-400.

Bell, G. H., D. P. Cuthbertson, and J. Orr. 1941. Strength and size of bone in relation to calcium intake. *Journal of Physiology* 100: 299-317.

Bolander, M. E. 1992. Regulation of fracture repair by growth factors. *Proc. Soc. Exp. Biol. Med.* 200: 165-170.

Bonnarens, F. and T. A. Einhorn. 1984. Production of a standard closed fracture in laboratory animal bone. *J. Orthop. Res.* 2: 97-101.

Brighton, C. T., J. L. Schaffer, D. B. Shapiro, J. J. S. Tang, and C. C. Clark. 1991. Proliferation and macromolecular synthesis by rat calvarial bone cells grown in various oxygen tensions. *J. Orthop. Res.* 9: 847-854.

Cohen, R. B., G. V. Hahn, J. A. Tabas, J. Peeper, C. L. Levitz, A. Sando, N. Sando, M. Zasloff, and F. S. Kaplan. 1993. The natural history of heterotopic ossification in patients who have fibrodysplasia ossificans progressive. *J. Bone and Joint Surg.* 75-A: 215-219.

Davies, N. M., A. J. McLachlan, R. O. Day, and K. M. Williams. 2000. Clinical pharmacokinetics and pharmacodynamics of celecoxib: a selective cyclo-oxygenase-2 inhibitor. *Clinical Pharmacokinetics* 38: 225-242.

Dekel, S., G. Lenthall, and M. J. O. Francis. 1981. Release of prostaglandins from bone and muscle after tibial fracture. *J. Bone and Joint Surg.* 63-B: 185-189.

Depré, M., E. Ehrich, A. van Hecken, I. De Lepeleire, A. Dallob, P. Wong, A. Porras, B. J. Gertz, and P. J. De Schepper. 2000. Pharmacokinetics, COX-2 specificity, and tolerability of supratherapeutic doses of rofecoxib in humans. *European Journal of Pharmacology* 56: 167-174.

Einhorn, T. A. 1998. The cell and molecular biology of fracture healing. *Clin Orthop:* S7-21.

Engesaeter, L. B., A. Ekeland, and N. Langeland. 1978. Methods for testing the mechanical properties of the rat femur. *Acta. Orthop. Scand.* 49: 512-518.

Ferguson, C., E. Alpern, T. Miclau, and J. A. Helms. 1999. Does adult fracture repair recapitulate embryonic skeletal formation? *Mech. Dev.* 87: 57-66.

Feyen, J. H., G. van der Wilt, P. Moonen, A. Di Bon, and P. J. Nijweide. 1984. Stimulation of arachidonic acid metabolism in primary cultures of osteoblast-like cells by hormones and drugs. *Prostaglandins* 28: 769-781.

Halpin, R. A., L. A. Geer, K. E. Zhang, T. M. Marks, D. C. Dean, A. N. Jones, D. Melillo, G. Doss, and K. P. Vyas. 2000. The absorption, distribution, metabolism and excretion of rofecoxib, a potent and selective cyclooxygenase-2 inhibitor, in rats and dogs. *Drug Metabolism and Disposition* 28: 1244-1254.

Hsu, A.-L., T.-T. Ching, D.-S. Wang, X. Song, V. M. Rangnekar, and C.-S. Chen. 2000. The cyclooxygenase-2 inhibitor celecoxib induces apoptosis by blocking Akt activation in human prostate cancer cells independently of Bcl-2. *J. Biol. Chem.* 275: 11397-11403.

Jones, M. K., H. Wang, B. M. Peskar, E. Levin, R. M. Itani, I. J. Sarfeh, and A. S. Tamawski. 1999. Inhibition of angiogenesis by nonsteroidal anti-inflammatory drugs: insight into the mechansims and implications for cancer growth and ulcer healing. *Nat. Med.* 5: 1418-1423.

Kaplan, F. S., J. A. Tabas, F. H. Gannon, G. Finkel, G. V. Hahn, and M. A. Zasloff. 1993. The histopathology of fibrodysplasia ossificans progressiva: an endochondral process. *J. Bone and Joint Surg.* 75-A: 220-230.

Kawaguchi, H., C. C. Pilbeam, J. R. Harrison, and L. G. Raisz. 1995. The role of prostaglandins in the regulation of bone metabolism. *Clin. Orth. Rel. Res.* 313: 36-46.

Klein, D. C. and L. G. Raisz. 1970. Prostaglandins: stimulation of bone resorption in tissue culture. *Endocrinol* 86: 1436-1440.

Klein-Nulend, J., E. H. Burger, C. M. Semeins, L. G. Raisz, and C. C. Pilbeam. 1997. Pulsating fluid flow stimulates prostaglandin release and inducible prostaglandin G/H synthase mRNA expression in primary mouse bone cells. *J. Bone Miner. Res.* 12: 45-51.

Langenbach, R., S. G. Morham, H. F. Tiano, C. D. Loftin, B. I. Ghanayem, P. C. Chulada, J. F. Mahler, C. A. Lee, E. H. Goulding, K. D. Kluckman, H. S. Kim, and O. Smithies. 1995. Prostaglandin synthase 1 gene disruption in mice reduces arachidonic acid-induced inflammation and indomethacin-induced gastric ulceration. *Cell* 83: 483-492.

Maniatopoulos, C., A. Rodriguez, D. A. Deporter, and A. H. Melcher. 1986. An improved method for preparing histological sections of metallic implants. *International Journal of Oral and Maxillofacial Implants* 1: 31-37.

Masferrer, J. L., B. S. Zweifel, P. T. Manning, S. D. Hauser, K. M. Leahy, W. G. Smith, P. C. Isakson, and K. Seibert. 1994. Selective inhibition of inducible cyclooxygenase 2 in vivo is antiinflammatory and nonulcerogenic. *Proc. Natl. Acad. Sci. USA* 91: 3228-3232.

Moore, K. D., K. Goss, and J. O. Anglen. 1998. Indomethacin versus radiation therapy for prophylaxis against heterotopic ossification in acetabular fractures. *J. Bone and Joint Surg.* 80-B: 259-263.

Morham, S. G., R. Langenbach, C. D. Loftin, H. F. Tiano, N. Vouloumanos, J. C. Jennette, J. F. Mahler, K. D. Kluckman, A. Ledford, C. A. Lee, and O. Smithies. 1995. Prostaglandin synthase 2 gene disruption causes severe renal pathology in the mouse. *Cell* 83: 473-482.

Muscará, M. N., W. McKnight, S. Asfaha, and J. L. Wallace. 2000. Wound collagen deposition in rats: effects of an NO-NSAID and a selective COX-2 inhibitor. *British Journal of Pharmacology* 129: 681-686.

Needleman, P., J. Turk, B. A. Jakschik, A. R. Morrison, and J. B. Lefkowith. 1986. Arachidonic acid metabolism. *Ann. Rev. Biochem.* 55: 69-102.

Nicholls, P. J., E. Berg, F. E. Bliven, Jr., and J. M. Kling. 1979. X-ray diagnosis of healing fractures in rabbits. *Clin. Orth. Rel. Res.* 142: 234-236.

O'Banion, M. K., V. D. Winn, and D. A. Young. 1992. cDNA cloning and functional activity of a glucocorticoid-regulated inflammatory cyclooxygenase. *Proc. Natl. Acad. Sci. USA* 89: 4888-4892.

Okada, Y., J. A. Lorenzo, A. M. Freeman, M. Tomita, S. G. Morham, L. G. Raisz, and C. C. Pilbeam. 2000. Prostaglandin G/H synthase-2 is required for maximal formation of osteoclast-like cells in culture. *J. Clin. Invest.* 105: 823-832.

O'Sullivan, M. G., F. H. Chilton, E. M. Huggins, Jr., and C. E. McCall. 1992a. Lipopolysaccharide priming of alveolar macrophages for enhanced synthesis of prostanoids involves induction of a novel prostaglandin H synthase. *J. Biol. Chem.* 267: 14547-14550.

O'Sullivan, M. G., E. M. Huggins, Jr., E. A. Meade, D. L. DeWitt, and C. E. McCall. 1992b. Lipopolysaccharide induces prostaglandin H synthase-2 in alveolar macrophages. *Biochem. Biophys. Res. Comm.* 187: 1123-1127.

Panjabi, M. M., R. W. Lindsey, S. D. Walter, and A. A. White, 3rd. 1989. The clinician's ability to evaluate the strength of healing fractures from plain radiographs. *J. Orthop. Trauma* 3: 29-32.

Paulson, S. K., J. Y. Zhang, A. P. Breau, J. D. Hribar, N. W. K. Liu, S. M. Jessen, Y. M. Lawal, J. N. Cogburn, C. J. Gresk, C. S. Markos, T. J. Maziasz, G. L. Schoenhard, and E. G. Burton. 2000. Pharmacokinetics, tissue distribution, metabolism, and excretion of celecoxib in rats. *Drug Metabolism and Disposition* 28: 514-521.

Popov, E. P. 1968. *Introduction to mechanics of solids.* Prentice-Hall, Inc., Englewood Cliffs, N.J.

Pritchett, J. W. 1995. Ketorolac prophylaxis against heterotopic ossification after hip replacement. *Clin. Orth. Rel. Res.* 314: 162-165.

Raskin, J. B. 1999. Gastrointestinal effects of nonsteroidal anti-inflammatory therapy. *Am. J. Med.* 106(5B): 3S-12S.

Riendeau, D., M. D. Percival, C. Brideau, S. Charleson, D. Dube, D. Ethier, J.-P. Falgueyret, R. W. Friesen, R. Gordon, G. Greig, J. Guay, J. Mancini, M. Ouellet, E. Wong, L. Xu, S. Boyce, D. Visco, Y. Girard, P. Prasit, R. Zamboni, I. W. Rodger, M. Gresser, A. W. Ford-Hutchinson, R. N. Young, and C.-C. Chan. 2001. Etoricoxib (MK-0663): preclinical profile and comparison with other agents that selectively inhibit cyclooxygenase-2. *Journal of Pharmacology and Experimental Therapeutics* 296: 558-566.

Rø, J., N. Langeland, and J. Sander. 1978. Effect of indomethacin on collagen metabolism of rat fracture callus in vitro. *Acta. Orthop. Scand.* 49: 323-328.

Rø, J., E. Sudmann, and P. F. Marton. 1976. Effect of indomethacin on fracture healing in rats. *Acta. Orthop. Scand.* 47: 588-599.

Rossi, A., P. Kapahi, G. Natoli, T. Takahashi, Y. Chen, M. Karin, and M. G. Santoro. 2000. Anti-inflammatory cylopentenone prostaglandins are direct inhibitors of IκB kinase. *Nature* 403: 103-108.

Shigeta, J.-I., S. Takahashi, and S. Okabe. 1998. Role of cyclooxygenase-2 in the healing of gastric ulcers in rats. *Journal of Pharmacology and Experimental Therapeutics* 286: 1383-1390.

Topper, J. N., J. Cai, D. Falb, and M. A. Gimbrone, Jr. 1996. Identification of vascular endothelial genes differentially responsive to fluid mechanical stimuli: cyclooxygenase-2, manganese superoxide dismutase, and endothelial cell nitric oxide synthase are selectively up-regulated by steady larninar shear stress. *Proc. Natl. Acad. Sci. USA* 93: 10417-10422.

Vane, J. R., Y. S. Bakhle, and R. M. Botting. 1998. Cyclooxygenase 1 and 2. *Annual Review of Pharmacology and Toxicology* 38: 97-120.

Vortkamp, A., S. Pathi, G. M. Peretti, E. M. Caruso, D. J. Zaleske, and C. J. Tabin. 1998. Recapitulation of signals regulating embryonic bone formation during postnatal growth and fracture repair. *Mech. Dev.* 71: 65-76.

Wadleigh, D. J. and H. R. Herschman. 1999. Transcriptional regulation of the cyclooxygenase-2 gene by diverse ligands in murine osteoblasts. *Biochem. Biophys. Res. Comm.* 264: 865-870.

Wallace, J. L., A. Bak, W. McKnight, S. Asfaha, K. A. Sharkey, and W. K. MacNaughton. 1998. Cyclooxygenase 1 contributes to inflammatory responses in rats and mice: implications for gastrointestinal toxicity. *Gastroenterology* 115: 101-109.

Warner, T. D., F. Giuliano, I. Vojnovic, A. Bukasa, J. A. Mitchell, and J. R. Vane. 1999. Nonsteroid drug selectivities for cyclo-oxygenase-1 rather than cyclo-oxygenase-2 are associated with human gastrointestinal toxicity: a full in vitro analysis. *Proc. Natl. Acad. Sci. USA* 96: 7563-7568.

Whelton, A. 1999. Nephrotoxicity of nonsteroidal anti-inflammatory drugs: physiological foundations and clinical implications. *Am. J. Med.* 106(5B): 13S-24S.

White, A. A., III, M. M. Panjabi, and W. O. Southwick. 1977. The four biomechanical stages of fracture repair. *J. Bone and Joint Surg.* 59-A: 188-192.

Xie, W., J. G. Chipman, D. L. Robertson, R. L. Erikson, and D. L. Simmons. 1991. Expression of a mitogen-responsive gene encoding prostaglandin synthase is regulated by mRNA splicing. *Proc. Natl. Acad. Sci. USA* 88: 2692-2696.

Zhang, X., S. G. Morham, R. Langenbach, R. B. Baggs, and D. A. Young. 2000. Lack of cyclooxygenase-2 inhibits growth of teratocarcinomas in mice. *Exp. Cell Res.* 254: 232-240.

TABLE 3

(SEQ. ID. NO.1)
I. HUMAN COX-1 cDNA SEQUENCE

```
GCGCCATGAGCCGGAGTCTCTTGCTCCGGTTCTTGCTGTTCCTGCTCCTG

CTCCCGCCGCTCCCCGTCCTGCTCGCGGACCCAGGGGCGCCCACGCCAGT

GAATCCCTGTTGTTACTATCCATGCCAGCACCAGGGCATCTGTGTCCGCT

TCGGCCTTGACCGCTACCAGTGTGACTGCACCCGCACGGGCTATTCCGGC

CCCAACTGCACCATCCCTGGCCTGTGGACCTGGCTCCGGAATTCACTGCG

GCCCAGCCCCTCTTTCACCCACTTCCTGCTCACTCACGGGCGCTGGTTCT

GGGAGTTTGTCAATGCCACCTTCATCCGAGAGATGCTCATGCGCCTGGTA

CTCACAGTGCGCTCCAACCTTATCCCCAGTCCCCCCACCTACAACTCAGC

ACATGACTACATCAGCTGGGAGTCTTTCTCCAACGTGAGCTATTACACTC
```

TABLE 1

Torsional Mechanical Testing Data

Fractured Femur Data (not normalized to contralateral control femur)

| | All Contralateral Control Femurs | No Drug | | | Indomethacin | | | Celecoxib | | | Rofecoxib | | |
|---|---|---|---|---|---|---|---|---|---|---|---|---|---|
| | | 4 wks | 6 wks | 8 wks | 4 wks | 6 wks | 8 wks | 4 wks | 6 wks | 8 wks | 4 wks | 6 wks | 8 wks |
| Peak Torque (Tmax) in Nmm | | | | | | | | | | | | | |
| Mean | 716 | 452 | 430 | 643 | 417 | 357 | 469 | 302 | 567 | 620 | 250 | 383 | 338 |
| CV | 28 | 21 | 29 | 28 | 52 | 37 | 56 | 44 | 34 | 49 | 53 | 33 | 36 |
| Significance | — | — | — | — | 0.69 | 0.36 | 0.16 | 0.03 | 0.15 | 0.88 | 0.01 | 0.54 | 0.01 |
| Torsional Rigidity [(Tmax · L)/φ] | | | | | | | | | | | | | |
| Mean | 83,050 | 27,200 | 66,068 | 56,506 | 21,913 | 28,658 | 57,630 | 13,866 | 43,189 | 59,256 | 12,338 | 21,231 | 25,026 |
| CV | 35 | 48 | 17 | 20 | 46 | 57 | 55 | 53 | 77 | 22 | 59 | 51 | 69 |
| Significance | — | — | — | — | 0.43 | <0.01 | 0.93 | 0.06 | 0.11 | 0.69 | 0.04 | <0.01 | 0.01 |
| Shear Stress [(Tmax. · φ)/J] | | | | | | | | | | | | | |
| mean | 145 | 33 | 35 | 56 | 25 | 22 | 47 | 25 | 44 | 67 | 15 | 24 | 25 |
| CV | 38 | 42 | 34 | 27 | 85 | 47 | 66 | 73 | 73 | 41 | 58 | 41 | 48 |
| Significance | — | — | — | — | 0.42 | 0.08 | 0.48 | 0.37 | 0.47 | 0.40 | 0.03 | 0.13 | <0.01 |
| Shear Modulus (GPa) | | | | | | | | | | | | | |
| Mean | 6.9 | 0.4 | 1.5 | 1.3 | 0.3 | 0.4 | 1.8 | 0.3 | 0.9 | 1.7 | 0.2 | 0.3 | 0.5 |
| CV | 54 | 58 | 71 | 38 | 78 | 73 | 99 | 77 | 116 | 27 | 49 | 56 | 91 |
| Significance | — | — | — | — | 0.33 | 0.08 | 0.46 | 0.26 | 0.40 | 0.16 | 0.04 | 0.07 | 0.01 |
| Sample Size | 81 | 6 | 5 | 7 | 8 | 7 | 8 | 8 | 8 | 6 | 6 | 7 | 5 |

CV: Coefficient of Variation (standard deviation as a percentage).
Significance: Comparisons were made using a standard two-tailed T-test between the no drug fractured femur values and the experimental fractured femur values within a time point. These comparisons were not made between data normalized with the contralateral control femur as shown in FIG. 3.

TABLE 2

Frequency of Unions, Mal-Unions, and Non-Unions in the Mechanically Tested Fractured Femurs at 8 weeks Post-Fracture

| | Union (Stage IV)* | Mal-Union (Stage III) | Non-Union (Stage I/II) | $\chi^2$ P-value** |
|---|---|---|---|---|
| No Drugs | 7 | 0 | 0 | 0.338 |
| Indomethacin | 6 | 1 | 1 | — |
| Celecoxib | 0 | 3 | 3 | <0.001 |
| Rofecoxib | 0 | 1 | 4 | <0.001 |

*Classification scheme as described by White et al. (1977)
**Comparisons were made to the indomethacin treatment group data.

TABLE 3-continued

```
GTATTCTGCCCTCTGTGCCTAAAGATTGCCCCACACCCATGGGAACCAAA

GGGAAGAAGCAGTTGCCAGATGCCCAGCTCCTGGCCCGCCGCTTCCTGCT

CAGGAGGAAGTTCATACCTGACCCCCAAGGCACCAACCTCATGTTTGCCT

TCTTTGCACAACACTTCACCCACCAGTTCTTCAAAACTTCTGGCAAGATG

GGTCCTGGCTTCACCAAGGCCTTGGGCCATGGGGTAGACCTCGGCCACAT

TTATGGAGACAATCTGGAGCGTCAGTATCAACTGCGGCTCTTTAAGGATG

GGAAACTCAAGTACCAGGTGCTGGATGGAGAAATGTACCCGCCCTCGGTA
```

TABLE 3-continued

GAAGAGGCGCCTGTGTTGATGCACTACCCCCGAGGCATCCCGCCCCAGAG
CCAGATGGCTGTGGGCCAGGAGGTGTTTGGGCTGCTTCCTGGGCTCATGC
TGTATGCCACGCTCTGGCTACGTGAGCACAACCGTGTGTGTGACCTGCTG
AAGGCTGAGCACCCCACCTGGGGCGATGAGCAGCTTTTCCAGACGACCCG
CCTCATCCTCATAGGGGAGACCATCAAGATTGTCATCGAGGAGTACGTGC
AGCAGCTGAGTGGCTATTTCCTGCAGCTGAAATTTGACCCAGAGCTGCTG
TTCGGTGTCCAGTTCCAATACCGCAACCGCATTGCCATGGAGTTCAACCA
TCTCTACCACTGGCACCCCCTCATGCCTGACTCCTTCAAGGTGGGCTCCC
AGGAGTACAGCTACGAGCAGTTCTTGTTCAACACCTCCATGTTGGTGGAC
TATGGGGTTGAGGCCCTGGTGGATGCCTTCTCTCGCCAGATTGCTGGCCG
GATCGGTGGGGCAGGAACATGGACCACCACATCCTGCATGTGGCTGTGG
ATGTCATCAGGGAGTCTCGGGAGATGCGGCTGCAGCCCTTCAATGAGTAC
CGCAAGAGGTTTGGCATGAAACCCTACACCTCCTTCCAGGAGCTCGTAGG
AGAGAAGGAGATGGCAGCAGAGTTGGAGGAATTGTATGGAGACATTGATG
CGTTGGAGTTCTACCCTGGACTGCTTCTTGAAAAGTGCCATCCAAACTCT
ATCTTTGGGGAGAGTATGATAGAGATTGGGGCTCCCTTTTCCCTCAAGGG
TCTCCTAGGGAATCCCATCTGTTCTCCGGAGTACTGGAAGCCGAGCACAT
TTGGCGGCGAGGTGGGCTTTAACATTGTCAAGACGGCCACACTGAAGAAG
CTGGTCTGCCTCAACACCAAGACCTGTCCCTACGTTTCCTTCCGTGTGCC
GGATGCCAGTCAGGATGATGGGCCTGCTGTGGAGCGACCATCCACAGAGC
TCTGAGGGGCAGGAAAGCAGCATTCTGGAGGGGAGAGCTTTGTGCTTGTC
ATTCCAGAGTGCTGAGGCCAGGGCTGATGGTCTTAAATGCTCATTTTCTG
GTTTGGCATGGTGAGTGTTGGGGTTGACATTTAGAACTTTAAGTCTCACC
CATTATCTGGAATATTGTGATTCTGTTTATTCTTCCAGAATGCTGAACTC
CTTGTTAGCCCTTCAGATTGTTAGGAGTGGTTCTCATTTGGTCTGCCAGA
ATACTGGGTTCTTAGTTGACAACCTAGAATGTCAGATTTCTGGTTGATTT
GTAACACAGTCATTCTAGGATGTGGAGCTACTGATGAAATCTGCTAGAAA
GTTAGGGGTTCTTATTTTGCATTCCAGAATCTTGACTTTCTGATTGGTG
ATTCAAAGTGTTGTGTTCCCTGGCTGATGATCCAGAACAGTGGCTCGTAT
CCCAAATCTGTCAGCATCTGGCTGTCTAGAATGTGGATTTGATTCATTTT
CCTGTTCAGTGAGATATCATAGAGACGGAGATCCTAAGGTCCAACAAGAA
TGCATTCCCTGAATCTGTGCCTGCACTGAGAGGGCAAGGAAGTGGGGTGT
TCTTCTTGGGACCCCCACTAAGACCCTGGTCTGAGGATGTAGAGAGAACA
GGTGGGCTGTATTCACGCCATTGGTTGGAAGCTACCAGAGCTCTATCCCC
ATCCAGGTCTTGACTCATGGCAGCTGTTTCTCATGAAGCTAATAAAATTC
GCCC (SEQ. ID. NO.2)

II. HUMAN COX-2 cDNA SEQUENCE
CAATTGTCATACGACTTGCAGTGAGCGTCAGGAGCACGTCCAGGAACTCC
TCAGCAGCGCCTCCTTCAGCTCCACAGCCAGACGCCCTCAGACAGCAAAG
CCTACCCCCGCGCCGCGCCCTGCCCGCCGCTCGGATGCTCGCCCGCGCCC

TABLE 3-continued

TGCTGCTGTGCGCGGTCCTGGCGCTCAGCCATACAGCAAATCCTTGCTGT
TCCCACCCATGTCAAAACCGAGGTGTATGTATGAGTGTGGGATTTGACCA
GTATAAGTGCGATTGTACCCGGACAGGATTCTATGGAGAAAACTGCTCAA
CACCGGAATTTTTGACAAGAATAAAATTATTTCTGAAACCCACTCCAAAC
ACAGTGCACTACATACTTACCCACTTCAAGGGATTTTGGAACGTTGTGAA
TAACATTCCCTTCCTTCGAAATGCAATTATGAGTTATGTCTTGACATCCA
GATCACATTTGATTGACAGTCCACCAACTTACAATGCTGACTATGGCTAC
AAAAGCTGGGAAGCCTTCTCTAACCTCTCCTATTATACTAGAGCCCTTCC
TCCTGTGCCTGATGATTGCCCGACTCCCTTGGGTGTCAAAGGTAAAAAGC
AGCTTCCTGATTCAAATGAGATTGTGGAAAAATTGCTTCTAAGAAGAAAG
TTCATCCCTGATCCCCAGGGCTCAAACATGATGTTTGCATTCTTTGCCCA
GCACTTCACGCATCAGTTTTTCAAGACAGATCATAAGCGAGGGCCAGCTT
TCACCAACGGGCTGGGCCATGGGGTGGACTTAAATCATATTTACGGTGAA
ACTCTGGCTAGACAGCGTAAACTGCGCCTTTTCAAGGATGGAAAAATGAA
ATATCAGATAATTGATGGAGAGATGTATCCTCCCACAGTCAAAGATACTC
AGGCAGAGATGATCTACCCTCCTCAAGTCCCTGAGCATCTACGGTTTGCT
GTGGGGCAGGAGGTCTTTGGTCTGGTGCCTGGTCTGATGATGTATGCCAC
AATCTGGCTGCGGGAACACAACAGAGTATGCGATGTGCTTAAACAGGAGC
ATCCTGAATGGGGTGATGAGCAGTTGTTCCAGACAAGCAGGCTAATACTG
ATAGGAGAGACTATTAAGATTGTGATTGAAGATTATGTGCAACACTTGAG
TGGCTATCACTTCAAACTGAAATTTGACCCAGAACTACTTTTCAACAAAC
AATTCCAGTACCAAAATCGTATTGCTGCTGAATTTAACACCCTCTATCAC
TGGCATCCCCTTCTGCCTGACACCTTTCAAATTCATGACCAGAAATACAA
CTATCAACAGTTTATCTACAACAACTCTATATTGCTGGAACATGGAATTA
CCCAGTTTGTTGAATCATTCACCAGGCAAATTGCTGGCAGGGTTGCTGGT
GGTAGGAATGTTCCACCCGCAGTACAGAAAGTATCACAGGCTTCCATTGA
CCAGAGCAGGCAGATGAAATACCAGTCTTTTAATGAGTACCGCAAACGCT
TTATGCTGAAGCCCTATGAATCATTTGAAGAACTTACAGGAGAAAAGGAA
ATGTCTGCAGAGTTGGAAGCACTCTATGGTGACATCGATGCTGTGGAGCT
GTATCCTGCCCTTCTGGTAGAAAAGCCTCGGCCAGATGCCATCTTTGGTG
AAACCATGGTAGAAGTTGGAGCACCATTCTCCTTGAAAGGACTTATGGGT
AATGTTATATGTTCTCCTGCCTACTGGAAGCCAAGCACTTTTGGTGGAGA
AGTGGGTTTTCAAATCATCAACACTGCCTCAATTCAGTCTCTCATCTGCA
ATAACGTGAAGGGCTGTCCCTTTACTTCATTCAGTGTTCCAGATCCAGAG
CTCATTAAAACAGTCACCATCAATGCAAGTTCTTCCCGCTCCGGACTAGA
TGATATCAATCCCACAGTACTACTAAAAGAACGTTCGACTGAACTGTAGA
AGTCTAATGATCATATTTATTTATTTATATGAACCATGTCTATTAATTTA
ATTATTTAATAATATTTATATTAAACTCCTTATGTTACTTAACATCTTCT
GTAACAGAAGTCAGTACTCCTGTTGCGGAGAAAGGAGTCATACTTGTGAA

TABLE 3-continued

```
GACTTTTATGTCACTACTCTAAAGATTTTGCTGTTGCTGTTAAGTTTGGA
AAACAGTTTTTATTCTGTTTTATAAACCAGAGAGAAATGAGTTTTGACGT
CTTTTTACTTGAATTACTATCACAAGATGGCAAAATGCTGAAAGTTTTTA
CACTGTCGATGTTTCCAATGCATCTTCCATGATGCATTAGAAGTAACTAA
TGTTTGAAATTTTAAAGTACTTTTGGTTATTTTTCTGTCATCAAACAAAA
ACAGGTATCAGTGCATTATTAAATGAATATTTAAATTAGACATTACCAGT
AATTTCATGTCTACTTTTTAAAAATCAGCAATGAAACAATAATTTGAAATT
TCTAAATTCATAGGGTAGAATCACCTGTAAAAGCTTGTTTGATTTCTTAA
AGTTATTAAACTTGTACATATACCAAAAAGAAGCTGTCTTGGATTTAAAT
CTGTAAAATCAGATGAAATTTTACTACAATTGCTTGTTAAAATATTTTAT
AAGTGATGTTCCTTTTTCACCAAGAGTATAAACCTTTTTAGTGTGACTGT
TAAAACTTCCTTTTAAATCAAAATGCCAAATTTATTAAGGTGGTGGAGCC
ACTGCAGTGTTATCTCAAAATAAGAATATTTTGTTGAGATATTCCAGAAT
TTGTTTATATGGCTGGTAACATGTAAAATCTATATCAGCAAAAGGGTCTA
CCTTTAAAATAAGCAATAACAAAGAAGAAAACCAAATTATTGTTCAAATT
TAGGTTTAAACTTTTGAAGCAAACTTTTTTTTATCCTTGTGCACTGCAGG
CCTGGTACTCAGATTTTGCTATGAGGTTAATGAAGTACCAAGCTGTGCTT
GAATAACGATATGTTTTCTCAGATTTTCTGTTGTACAGTTTAATTTAGCA
GTCCATATCACATTGCAAAAGTAGCAATGACCTCATAAAATACCTCTTCA
AAATGCTTAAATTCATTTCACACATTAATTTTATCTCAGTCTTGAAGCCA
ATTCAGTAGGTGCATTGGAATCAAGCCTGGCTACCTGCATGCTGTTCCTT
TTCTTTTCTTCTTTTAGCCATTTTGCTAAGAGACACAGTCTTCTCATCAC
TTCGTTTCTCCTATTTTGTTTTACTAGTTTTAAGATCAGAGTTCACTTTC
TTTGGACTCTGCCTATATTTTCTTACCTGAACTTTTGCAAGTTTTCAGGT
AAACCTCAGCTCAGGACTGCTATTTAGCTCCTCTTAAGAAGATTAAAAGA
GAAAAAAAAGGCCCTTTTAAAAATAGTATACACTTATTTTAAGTGAAAA
GCAGAGAATTTTATTTATAGCTAATTTTAGCTATCTGTAACCAAGATGGA
TGCAAAGAGGCTAGTGCCTCAGAGAGAACGCCCTTCTTATTTAAAAACA
AAACCAAATGATATCTAAGTAGTTCTCAGCAATAATAATAATGACGATAA
TACTTCTTTTCCACATCTCATTGTCACTGACATTTAATGGTACTGTATAT
TACTTAATTTATTGAAGATTATTATTTATGTCTTATTAGGACACTATGGT
TATAAACTGTGTTTAAGCCTACAATCATTGATTTTTTTTGTTATGTCAC
AATCAGTATATTTTCTTTGGGGTTACCTCTCTGAATATTATGTAAACAAT
CCAAAGAAATGATTGTATTAAGATTTGTGAATAAATTTTAGAAATCTGA
TTGGCATATTGAGATATTTAAGGTTGAATGTTTGTCCTTAGGATAGGCCT
ATGTGCTAGCCCACAAAGAATATTGTCTCATTAGCCTGAATGTGCCATAA
GACTGACCTTTTAAAATGTTTTGAGGGATCTGTGGATGCTTCGTTAATTT
GTTCAGCCACAATTTATTGAGAAAATATTCTGTGTCAAGCACTGTGGGTT
TTAATATTTTTAAATCAAACGCTGATTACAGATAATAGTATTTATATAAA
TAATTGAAAAAATTTTCTTTTGGGAAGAGGGAGAAAATGAAATAAATATC
ATTAAAGATAACTCAGGAGAATCTTCTTTACAATTTTACGTTTAGAATGT
TTAAGGTTAAGAAAGAAATAGTCAATATGCTTGTATAAAACACTGTTCAC
TGTTTTTTTTAAAAAAAAAACTTGATTTGTTATTAACATTGATCTGCTGA
CAAAACCTGGGAATTTGGGTTGTGTATGCGAATGTTTCAGTGCCTCAGAC
AAATGTGTATTTAACTTATGTAAAAGATAAGTCTGGAAATAAATGTCTGT
TTATTTTTGTACTATTTA
```

(SEQ. ID. NO. 3)

III. HUMAN COX-1 AMINO ACID SEQUENCE

```
MSRSLLLRFLLFLLLLPPLPVLLADPGAPTPVNPCCYYPCQHQGICVRFG
LDRYQCDCTRTGYSGPNCTIPGLWTWLRNSLRPSPSFTHFLLTFGRWFWE
FVNATFIREMLMRLVLTVRSNLIPSPPTYNSAHDYISWESFSNVSYYTRI
LPSVPKDCPTPMGTKGKKQLPDAQLLARRFLLRRKFIPDPQGTNLMFAFF
AQHFTHQFFKTSGKMGPGFTKALGHGVDLGHIYGDNLERQYQLRLFKDGK
LKYQVLDGEMYPPSVEEAPVLMHYPRGIPPQSQMAVGQEVFGLLPGLMLY
ATLWLREHNRVCDLLKAEHPTWGDEQLFQTTRLILIGETIKIVIEEYVQQ
LSGYFLQLKFDPELLFGVQFQYRNRIAMEFNHLYHWHPLMPDSFKVGSQE
YSYEQFLFNTSMLVDYGVEALVDAFSRQIAGRIGGGRNMDHHILHVAVDV
IRESREMRLQPFNEYRKRFGMKPYTSFQELVGEKEMAAELEELYGDIDAL
EFYPGLLLEKCHPNSIFGESMIEIGAPFSLKGLLGNPICSPEYWKPSTFG
GEVGFNIVKTATLKKLVCLNTKTCPYVSFRVPDASQDDGPAVERPSTEL
```

(SEQ. ID. NO. 4)

IV. HUMAN COX-2 AMINO ACID SEQUENCE

```
MLARALLLCAVLALSHTANPCCSHPCQNRGVCMSVGFDQYKCDCTRTGFY
GENCSTPEFLTRIKLFLKPTPNTVHYILTHFKGFWNVVNNIPFLRNAIMS
YVLTSRSHLIDSPPTYNADYGYKSWEAFSNLSYYTRALPPVPDDCPTPLG
VKGKKQLPDSNEIVEKLLLRRKFIPDPQGSNMMFAFFAQHFTHQFFKTDH
KRGPAFTNGLGHGVDLNHIYGETLARQRKLRLFKDGKMKYQIIDGEMYPP
TVKDTQAEMIYPPQVPEHLRFAVGQEVFGLVPGLMMYATIWLREHNRVCD
VLKQEHPEWGDEQLFQTSRLILIGETIKIVIEDYVQHLSGYHFKLKFDPE
LLFNKQFQYQNRIAAEFNTLYHWHPLLPDTFQIHDQKYNYQQFIYNNSIL
LEHGITQFVESFTRQIAGRVAGGRNVPPAVQKVSQASIDQSRQMKYQSFN
EYRKRFMLKPYESFEELTGEKEMSAELEALYGDIDAVELYPALLVEKPRP
DAIFGETMVEVGAPFSLKGLMGNVICSPAYWKPSTFGGEVGFQIINTASI
QSLICNNVKGCPFTSFSVPDPELIKTVTINASSSRSGLDDINPTVLLKER
STEL
```

TABLE 4

(SEQ. ID. NO. 5)

I. MOUSE COX-1 cDNA SEQUENCE

```
GCCGTTGGCATTGCACATCCATCCACTCCCAGAGTCATGAGTCGAAGGAG
TCTCTCGCTCTGGTTTCCCCTGCTGCTGCTCCTGCTGCTGCCGCCGACAC
CCTCGGTCCTGCTCGCAGATCCTGGGGTGCCCTCACCAGTCAATCCCTGT
```

TABLE 4-continued

TGTTACTATCCGTGCCAGAACCAGGGTGTCTGTGTCCGCTTTGGCCTCGA
CAACTACCAGTGTGATTGTACTCGCACGGGCTACTCAGGCCCCAACTGTA
CCATCCCTGAGATCTGGACCTGGCTTCGGAATTCTCTGCGGCCCAGCCCC
TCGTTCACCCATTTCCTGCTGACACATGGATACTGGCTCTGGGAATTTGT
GAATGCCACCTTCATCCGAGAAGTACTCATGCGCCTGGTACTCACAGTGC
GGTCCAACCTTATCCCCAGCCCTCCGACCTACAACTCAGCGCATGACTAC
ATCAGCTGGGAGTCCTTCTCCAATGTGAGCTACTATACTCGCATTCTGCC
CTCTGTACCCAAAGACTGCCCCACACCCATGGGGACCAAAGGGAAGAAAC
AGTTACCAGATGTTCAGCTTCTGGCCCAACAGCTGCTGCTGAGAAGGGAG
TTCATTCCTGCCCCCAGGGCACCAACATCCTGTTTGCCTTCTTTGCACA
ACACTTCACCCACCAGTTCTTCAAGACCTCTGGAAAGATGGGTCCTGGCT
TTACCAAGGCCTTAGGCCACGGGGTAGACCTTGGCCACATTTATGGAGAT
AATCTGGAACGACAGTATCACCTGCGGCTCTTCAAGGATGGGAAACTTAA
GTACCAGGTGCTGGACGGAGAGGTGTACCCACCTTCCGTGGAACAGGCGT
CCGTGTTGATGCGCTACCCACCAGGTGTCCCGCCTGAAAGGCAGATGGCT
GTGGGCCAGGAGGTGTTTGGGTTGCTTCCGGGGCTGATGCTCTTCTCCAC
GATCTGGCTTCGTGAACATAACCGCGTGTGCGACCTGCTGAAGGAGGAGC
ATCCCACGTGGGATGATGAGCAGCTCTTCCAGACCACTCGCCTCATCCTT
ATAGGAGAAACCATCAAAATTGTCATTGAGGAGTATGTGCAGCACTTGAG
TGGCTATTTCCTGCAGCTCAAGTTTGACCCGGAGCTGCTGTTCCGAGCCC
AGTTCCAATATCGAAACCGCATCGCCATGGAATTTAACCATCTCTATCAC
TGGCATCCACTCATGCCCAACTCCTTCCAAGTGGGCTCACAAGAGTACAG
CTACGAGCAGTTTTTATTTAACACTTCTATGCTGGTGGACTATGGGGTTG
AGGCACTGGTGGATGCCTTCTCTCGCCAGAGGGCTGGCCGGATTGGTGGA
GGTAGGAACTTTGACTATCATGTTCTGCATGTGGCTGTGGATGTCATCAA
GGAGTCCCGAGAGATGCGCCTACAGCCCTTCAATGAATACCGAAAGAGGT
TTGGCTTGAAGCCTTACACCTCTTTCCAGGAGCTCACAGGAGAGAAGGAG
ATGGCTGCTGAGTTGGAGGAGCTGTACGGTGACATCGATGCTTTAGAGTT
CTACCCGGGGTTGCTGCTGGAGAAGTGCCAGCCCAACTCCATCTTTGGAG
AAAGTATGATAGAGATGGGGGCTCCCTTTTCCCTCAAGGGCCTCCTAGGG
AATCCCATCTGTTCCCCAGAGTACTGGAAACCCAGCACGTTCGGTGGTGA
CGTGGGCTTCAACCTTGTCAACACAGCCTCACTGAAGAAACTGGTCTGCC
TCAACACCAAGACCTGCCCCTATGTTTCCTTCCGTGTGCCAGATTACCCT
GGAGATGACGGGTCTGTCTTAGTGAGACGCTCCACTGAGCTCTGAGGGAG
CTGGAAAGCAGCCTCTGGAGGGAGGAGTTTTGTTCCTGATGAAGACAAGT
CCTTGATGTGGGTTTTCGTGGCTTGGCATTGTGAGAGCTGATGCTCACAT
TTGAAACTTTGGGTCTTACCCTTGCCTAGAAAATTGTGATTTTGCCACTT
TCGGATGTTGAATTCTTTGTTAACTAAGAAAGTTAGAAGTGGTTTTGTCT
GCCTCCTCAGAACTTGGCTCTTTGTTGGCAACTCAGAAAGTCAGATTTCT

GGTTGATTTGGAATATAGGCTTAAAACTTTATATTATAGGGTAGGGTGTG
GTTGCACACACCTTAATCCCAGCACTTGGAAGGCAGAGGCAGTTGGATCT
CTGGGAGTTTGAGGCCAGTTTGGCCTATATAGTGAGTTCTAGGCCAGCCA
TGGATGCATAGTGAGACTCTTTCTCAAAACAAACAAACAAACAAACAAAC
AAACAACTTTTAGAATGTAGAATTCCGTAAAAAAAAAAAATCCCTTGAAA
GTTAATGGGGTCCTCAATTTTCTTCCTAGAATTTGGAGGCCTCTTCAGAA
TGTTGACTATCTGACAGGTGACTCAGAAGGTCCTGTTCCTGGTCAATGAT
CTATAACATGGGCCAAAACATTCCCAACTTGAATGTCTAGAATGTGGAAT
TGGTTCATTTTCCTGTTCAGTGAAATGGACACAGAACAAAAGAACCCAGT
GTCCAGCAAGAATTGCCTTGCCCAAACCTACGTCTACGCCAAAGGTCAAG
GCAGTAAGGTGTTCTTGGGAGCCACACTTAGACTCTTTCCAAAGATGTGG
AGGGAACAGATGGACTCATCTATGATCTTGGTTGGAAACACCACAGTTC
TATCCCCATCCAGATCTTTGCTTGTGGCAGCTGTTTCTCATGAAGCTAAT
AAAATTC (SEQ. ID. NO.6)

II. MOUSE COX-2 cDNA SEQUENCE
AGTTGTCAAACTGCGAGCTAAGAGCTTCAGGAGTCAGTCAGGACTCTGCT
CACGAAGAATCTCAGCACTGCATCCTGCCAGCTCCACCGCCACCACCACT
GCCACCTCCGCTGCCACCTCTGCGATGCTCTTCCGAGCTGTGCTGCTCTG
CGCTGCCCTGGGGCTCAGCCAGGCAGCAAATCCTTGCTGTTCCAATCCAT
GTCAAAACCGTGGGGAATGTATGAGCACAGGATTTGACCAGTATAAGTGT
GACTGTACCCGGACTGGATTCTATGGTGAAAACTGTACTACACCTGAATT
TCTGACAAGAATCAAATTACTGCTGAAGCCCACCCCAAACACAGTGCACT
ACATCCTGACCCACTTCAAGGGAGTCTGGAACATTGTGAACAACATCCCC
TTCCTGCGAAGTTTAACTATGAAATATGTGCTGACATCCAGATCATATTT
GATTGACAGTCCACCTACTTACAATGTGCACTATGGTTACAAAAGCTGGG
AAGCTTCTCCAACCTCTCCTACTACACCAGGGCCCTTCCTCCAGTAGCA
GATGACTGCCCAACTCCCATGGGTGTGAAGGGAAATAAGGAGCTTCCTGA
TTCAAAAGAAGTGCTGGAAAAGGTTCTTCTACGAGAGAGTTCATCCCTG
ACCCCCAAGGCTCAAATATGATGTTTGCATTCTTTGCCCAGCACTTCACC
CATCAGTTTTTCAAGACAGATCATAAGCGAGGACCTGGGTTCACCCGAGG
ACTGGGCCATGGAGTGGACTTAAATCACATTTATGGTGAAACTCTGGACA
GACAACATAAACTGCGCCTTTTCAAGGATGGAAAATTGAAATATCAGGTC
ATTGGTGGAGAGGTGTATCCCCCCACAGTCAAAGACACTCAGGTAGAGAT
GATCTACCCTCCTCACATCCCTGAGAACCTGCAGTTTGCTGTGGGGCAGG
AAGTCTTTGGTCTGGTGCCTGGTCTGATGATGTATGCCACCATCTGGCTT
CGGGAGCACAACAGAGTGTGCGACATACTCAAGCAGGAGCATCCTGAGTG
GGGTGATGAGCAACTATTCCAAACCAGCAGACTCATACTCATAGGAGAGA
CTATCAAGATAGTGATCGAAGACTACGTGCAACACCTGAGCGGTTACCAC
TTCAAACTCAAGTTTGACCCAGAGCTCCTTTTCAACCAGCAGTTCCAGTA
TCAGAACCGCATTGCCTCTGAATTCAACACACTCTATCACTGGCACCCCC

TABLE 4-continued

```
TGCTGCCCGACACCTTCAACATTGAAGACCAGGAGTACAGCTTCAAACAG
TTTCTCTACAACAACTCCATCCTCCTGGAACATGGACTCACTCAGTTTGT
TGAGTCATTCACCAGACAGATTGCTGGCCGGGTTGCTGGGGAAGAAATG
TGCCAATTGCTGTACAAGCAGTGGCAAAGGCCTCCATTGACCAGAGCAGA
GAGATGAAATACCAGTCTCTCAATGAGTACCGCAAACGCTTCTCCCTGAA
GCCGTACACATCATTTGAAGAACTTACAGGAGAGAAGGAAATGGCTGCAG
AATTGAAAGCCCTCTACAGTGACATCGATGTCATGGAACTGTACCCTGCC
CTGCTGGTGGAAAAACCTCGTCCAGATGCTATCTTTGGGGAGACCATGGT
AGAGCTTGGAGCACCATTCTCCTTGAAAGGACTTATGGGAAATCCCATCT
GTTCTCCTCAATACTGGAAGCCGAGCACCTTTGGAGGCGAAGTGGGTTTT
AAGATCATCAATACTGCCTCAATTCAGTCTCTCATCTGCAATAATGTGAA
GGGGTGTCCCTTCACTTCTTTCAATGTGCAAGATCCACAGCCTACCAAAA
CAGCCACCATCAATGCAAGTGCCTCCCACTCCAGACTAGATGACATTAAC
CCTACAGTACTAATCAAAAGGCGTTCAACTGAGCTGTAAAAGTCTACTGA
CCATATTTATTTATTTATGTGAAGGAATTTAATTTAATTATTTAATATTT
ATACTGAATTTTTTTCATGTAACATCTTCCATAACAGAAGGCAATGTTC
TTGAACAATGTTACATTTGTGAAGATTCCTCCGGTGTTTGTCCTTTAAAT
ATGTGTTACCTGAAACTGAAAGGAAATCAGCATTCATTCCTCTACATAAG
CCAGTGAGAAGGGAAATGAATTTTGATATCTTTATACTTGAATTTCAGAT
CATGAATTAGCTTAACAAGAACCAAGGAAAATGTATGAATATGTGAGTG
TTGTTACAAGATGAAAATGCTGCAGGTATCAACACTGTTGGTTACACTG
TGTCTTCTTTACCTATGATAGGAGCATGTAATGTGGAATTCGTCTTAAAT
CCTTGCATATCTTTATCTCATCAAACAAAGGGGTCCAAGTTCAGTTTTAA
ATAAGCATTTAAGGCAGATACTGACAACAATCTCATTTTTTTAAAATGTT
GTCTTGAGACAAATAATTTGAAATTTCTAAATTGGGACGTTTGAATCACT
TTTGAAAGCTCTTACTTTCTTAAGCTGTCAGGTTTGTACCGACATGGAGT
AAACAGCTATCATAAACGTAAATCTCCAAAACTAGTAGAAATTATGTCAT
GATTGATGGTTAAGATACCATGTCAGGGATTGTCTTTTCTTAGAAGTAGT
GAAAGCTACTTACTATGACAATCAGACCTTCCTTGTATGTCAAAATGCTG
GTGTGGAAGGTGGTGGAGCCCGTGCTGCTCTGTCTTAACTATGAGTGTGA
GCTTTAAAGCTCGTTGATGAGTGGTAGCCAGCAAAGCCTAGAGCAACAAA
AGCGTTCTACAAAGGAACTAACCAAGAACAAAGAAGGGGTTCCCAATTAAA
GATCACATTCAGGGTTAAACTTCCAAAGGAGACATCCTGATCCTGGTTTT
GTGCTGGCCTGGTACTCAGTAGGTTTTTGCTGTGAGGTTAAAGACTTGCC
AGGGCTGAACTTCGAAACAGTTTTTCTGTTGCACAGTATGATGTAACAGT
CCATCTCTCAATGCAATAGGTATCAGTGGCCTCGTGAGCTTCTTCACAAT
ATTTGATATGTCTTCCAGCCCATTGAACCTGGACTGCAGAAGGCCCCATG
TCATGTGTGAGCTCAGCCTGGATGCCAGCATTTGCTGCTCCTCTTAGTTC
CGTTTCTCGTGGTCACTTTACTACGAGAAACGCTGATTGGGTTTTCGTAG
CTGTGTTACCAGGTTTTTAGTATCAGAACTATTCTTTCTTTAACCTCTAT
TCATATTTTCTCTACTTGAAGTTTTACATTCAGGAAAACCTCAGCGCTCA
GGACTACTATGTACCTCCCCTTTGGAGGGAAAAATTCATTTTTAGGTAAA
AGGCAAAAATTTTTAAAAATATTTTTTATTTATAATTATATGGAAGGGC
CCTACCAAGATGCTAGAAATATAGGGAGTTCCTGACAAGAAATTTCCATT
CTTATTCTGAAGAATTGCTTTCTTACTTAAAAACAAAGACAGTTTGTGAG
TAGTTCTGGGCAATAGGGATAAATATAAAACAATAATGATGATCATTTTC
TACATCTCATTATCAGCTGAGGTACTGTATATTACTGAATTTATTGAAGA
TAGTTATGTCTTTTAGACATTGTTGTTATAAACTATGTTTAAGCCTACTA
CAAGTGTTTCTTTTTTGCATTATGTTGGAATTGATGTACCTTTTTTATGA
TTACCTCTCTGAACTATGGTGTGAACAATCAAACAAAATGATGAGATTAA
CGTTCATGGATAAATTCTAAGAAAACTAGTGTATTTTTTGAAAAGTTTG
AAGTTAGAACTTAGGCTGTTGGAATTTACGCATAAAGCAGACTGCATAGG
ATCCAATATTGACTGACCCAAGCATGTTATAAAGACTGACATTTTAGACA
TTTTGAAGGCCCTGTAAGTGTTTATTAATTAGTTAGAACTTAATTGATTA
AAAAATATATCCAAAGCACTATAGGCATTAGAATTC
```
(SEQ. ID. NO.7)

III. MOUSE COX-1 AMINO ACID SEQUENCE
MSRRSLSLWFPLLLLLLLPPTPSVLLADPGVPSPVNPCCYYPCQNQGVCV
RFGLDNYQCDCTRTGYSGPNCTIPEIWTWLRNSLRPSPSFTHFLLTHGYW
LWEFVNATFIREVLMRLVLTVRSNLIPSPPTYNSAHDYISWESFSNVSYY
TRILPSVPKDCPTPMGTKGKKQLPDVQLLAQQLLLRREFIPAPQGTNILF
AFFAQHFTHQFFKTSGKMGPGFTKALGHGVDLGHIYGDNLERQYHLRLFK
DGKLKYQVLDGEVYPPSVEQASVLMRYPPGVPPERQMAVGQEVFGLLPGL
MLFSTIWLREHNRVCDLLKEEHPTWDDEQLFQTTRLILIGETIKIVIEEY
VQHLSGYFLQLKFDPELLFRAQFQYRNRIAMEFNHLYWHPLMPNSFQVG
SQEYSYEQFLFNTSMLVDYGVEALVDAFSRQRAGRIGGGRNFDYHVLHVA
VDVIKESREMRLQPFNEYRKRFGLKPYTSFQELTGEKEMAAELEELYGDI
DALEFYPGLLLEKCQPNSIFGESMIEMGAPFSLKGLLGNPICSPEYWKPS
TFGGDVGFNLVNTASLKKLVCLNTKTCPYVSFRVPDYPGDDGSVLVRRST
EL
(SEQ. ID. NO.8)

IV. MOUSE COX-2 AMINO ACID SEQUENCE
MLFRAVLLCAALGLSQAANPCCSNPCQNRGECMSTGFDQYKCDCTRTGFY
GENCTTPEFLTRIKLLLKPTPNTVHYILTHFKGVWNIVNNIPFLRSLTMK
YVLTSRSYLIDSPPTYNVHYGYKSWEAFSNLSYYTRALPPVADDCPTPMG
VKGNKELPDSKEVLEKVLLRREFIPDPQGSNMMFAFFAQHFTHQFFKTDH
KRGPGFTRGLGHGVDLNHIYGETLDRQHKLRLFKDGKLKYQVIGGEVYPP
TVKDTQVEMIYPPHIPENLQFAVGQEVFGLVPGLMMYATIWLREHNRVCD
ILKQEHPEWGDEQLFQTSRLILIGETIKIVIEDYVQHLSGYHFKLKFDPE
LLFNQQFQYQNRIASEFNTLYHWHPLLPDTFNIEDQEYSFKQFLYNNSIL
LEHGLTQFVESFTRQIAGRVAGGRNVPIAVQAVAKASIDQSREMKYQSLN
```

TABLE 4-continued

EYRKRFSLKPYTSFEELTGEKEMAAELKALYSDIDVMELYPALLVEKPRP

DAIFGETMVELGAPFSLKGLMGNPICSPQYWKPSTFGGEVGFKIINTASI

TABLE 4-continued

QSLICNNVKGCPFTSFNVQDPQPTKTATINASASHSRLDDINPTVLIKRR

STEL

SEQUENCE LISTING

<160> NUMBER OF SEQ ID NOS: 8

<210> SEQ ID NO 1
<211> LENGTH: 2554
<212> TYPE: DNA
<213> ORGANISM: Artificial sequence
<220> FEATURE:
<223> OTHER INFORMATION: Human COX-1 cDNA

<400> SEQUENCE: 1

| | | | | | |
|---|---|---|---|---|---|
| gcgccatgag | ccggagtctc | ttgctccggt | tcttgctgtt | cctgctcctg | ctcccgccgc | 60 |
| tccccgtcct | gctcgcggac | ccaggggcgc | ccacgccagt | gaatccctgt | tgttactatc | 120 |
| catgccagca | ccagggcatc | tgtgtccgct | tcggccttga | ccgctaccag | tgtgactgca | 180 |
| cccgcacggg | ctattccggc | cccaactgca | ccatccctgg | cctgtggacc | tggctccgga | 240 |
| attcactgcg | gcccagcccc | tctttcaccc | acttcctgct | cactcacggg | cgctggttct | 300 |
| gggagtttgt | caatgccacc | ttcatccgag | agatgctcat | gcgcctggta | ctcacagtgc | 360 |
| gctccaacct | tatccccagt | cccccccacct | acaactcagc | acatgactac | atcagctggg | 420 |
| agtctttctc | caacgtgagc | tattacactc | gtattctgcc | ctctgtgcct | aaagattgcc | 480 |
| ccacacccat | gggaaccaaa | gggaagaagc | agttgccaga | tgcccagctc | ctggcccgcc | 540 |
| gcttcctgct | caggaggaag | ttcatacctg | accccaagg | caccaacctc | atgtttgcct | 600 |
| tctttgcaca | acacttcacc | caccagttct | caaaacttc | tggcaagatg | ggtcctggct | 660 |
| tcaccaaggc | cttgggccat | ggggtagacc | tcggccacat | ttatggagac | aatctggagc | 720 |
| gtcagtatca | actgcggctc | tttaaggatg | gaaaactcaa | gtaccaggtg | ctggatggag | 780 |
| aaatgtaccc | gcctcggta | aagaggcgc | ctgtgttgat | gcactacccc | cgaggcatcc | 840 |
| cgccccagag | ccagatggct | gtgggccagg | aggtgttgg | gctgcttcct | gggctcatgc | 900 |
| tgtatgccac | gctctggcta | cgtgagcaca | accgtgtgtg | tgacctgctg | aaggctgagc | 960 |
| accccacctg | gggcgatgag | cagcttttcc | agacgacccg | cctcatcctc | ataggggaga | 1020 |
| ccatcaagat | tgtcatcgag | gagtacgtgc | agcagctgag | tggctatttc | ctgcagctga | 1080 |
| aatttgaccc | agagctgctg | ttcggtgtcc | agttccaata | ccgcaaccgc | attgccatgg | 1140 |
| agttcaacca | tctctaccac | tggcaccccc | tcatgcctga | ctccttcaag | gtgggctccc | 1200 |
| aggagtacag | ctacgagcag | ttcttgttca | acacctccat | gttggtggac | tatgggggttg | 1260 |
| aggccctggt | ggatgccttc | tctcgccaga | ttgctggccg | gatcggtggg | ggcaggaaca | 1320 |
| tggaccacca | catcctgcat | gtggctgtgg | atgtcatcag | ggagtctcgg | agatgcggc | 1380 |
| tgcagccctt | caatgagtac | cgcaagaggt | ttggcatgaa | accctacacc | tccttccagg | 1440 |
| agctcgtagg | agagaaggag | atggcagcag | agttggagga | attgtatgga | gacattgatg | 1500 |
| cgttggagtt | ctaccctgga | ctgcttcttg | aaaagtgcca | tccaaactct | atctttgggg | 1560 |
| agagtatgat | agagattggg | gctcccttt | ccctcaaggg | tctcctaggg | aatcccatct | 1620 |

-continued

| | |
|---|---|
| gttctccgga gtactggaag ccgagcacat ttggcggcga ggtgggcttt aacattgtca | 1680 |
| agacggccac actgaagaag ctggtctgcc tcaacaccaa gacctgtccc tacgtttcct | 1740 |
| tccgtgtgcc ggatgccagt caggatgatg ggcctgctgt ggagcgacca tccacagagc | 1800 |
| tctgagggc aggaaagcag cattctggag gggagagctt tgtgcttgtc attccagagt | 1860 |
| gctgaggcca gggctgatgg tcttaaatgc tcattttctg gtttggcatg gtgagtgttg | 1920 |
| gggttgacat ttagaacttt aagtctcacc cattatctgg aatattgtga ttctgttttat | 1980 |
| tcttccagaa tgctgaactc cttgttagcc cttcagattg ttaggagtgg ttctcatttg | 2040 |
| gtctgccaga atactgggtt cttagttgac aacctagaat gtcagatttc tggttgattt | 2100 |
| gtaacacagt cattctagga tgtggagcta ctgatgaaat ctgctagaaa gttaggggt | 2160 |
| tcttattttg cattccagaa tcttgacttt ctgattggtg attcaaagtg ttgtgttccc | 2220 |
| tggctgatga tccagaacag tggctcgtat cccaaatctg tcagcatctg ctgtctaga | 2280 |
| atgtggattt gattcatttt cctgttcagt gagatatcat agagacggag atcctaaggt | 2340 |
| ccaacaagaa tgcattccct gaatctgtgc ctgcactgag agggcaagga agtggggtgt | 2400 |
| tcttcttggg accccacta agaccctggt ctgaggatgt agagagaaca ggtgggctgt | 2460 |
| attcacgcca ttggttggaa gctaccagag ctctatcccc atccaggtct tgactcatgg | 2520 |
| cagctgtttc tcatgaagct aataaaattc gccc | 2554 |

<210> SEQ ID NO 2
<211> LENGTH: 4465
<212> TYPE: DNA
<213> ORGANISM: Artificial sequence
<220> FEATURE:
<223> OTHER INFORMATION: Human COX-2 cDNA

<400> SEQUENCE: 2

| | |
|---|---|
| caattgtcat acgacttgca gtgagcgtca ggagcacgtc caggaactcc tcagcagcgc | 60 |
| ctccttcagc tccacagcca gacgccctca gacagcaaag cctaccccg cgccgcgccc | 120 |
| tgcccgccgc tcggatgctc gcccgcgccc tgctgctgtg cgcggtcctg gcgctcagcc | 180 |
| atacagcaaa tccttgctgt tcccacccat gtcaaaaccg aggtgtatgt atgagtgtgg | 240 |
| gatttgacca gtataagtgc gattgtaccc ggacaggatt ctatggagaa aactgctcaa | 300 |
| caccggaatt tttgacaaga ataaaattat ttctgaaacc cactccaaac acagtgcact | 360 |
| acatacttac ccacttcaag ggattttgga acgttgtgaa taacattccc ttccttcgaa | 420 |
| atgcaattat gagttatgtc ttgacatcca gatcacattt gattgacagt ccaccaactt | 480 |
| acaatgctga ctatggctac aaaagctggg aagccttctc taacctctcc tattatacta | 540 |
| gagcccttcc tcctgtgcct gatgattgcc cgactccctt gggtgtcaaa ggtaaaaagc | 600 |
| agcttcctga ttcaaatgag attgtggaaa aattgcttct aagaagaaag ttcatccctg | 660 |
| atccccaggg ctcaaacatg atgtttgcat tctttgccca gcacttcacg catcagtttt | 720 |
| tcaagacaga tcataagcga gggccagctt tcaccaacgg gctgggccat ggggtggact | 780 |
| taaatcatat ttacggtgaa actctggcta gacagcgtaa actgcgcctt ttcaaggatg | 840 |
| gaaaaatgaa atatcagata attgatggag agatgtatcc tcccacagtc aaagatactc | 900 |
| aggcagagat gatctacccct cctcaagtcc ctgagcatct acggtttgct gtggggcagg | 960 |
| aggtctttgg tctggtgcct ggtctgatga tgtatgccac aatctggctg cgggaacaca | 1020 |
| acagagtatg cgatgtgctt aaacaggagc atcctgaatg gggtgatgag cagttgttcc | 1080 |
| agacaagcag gctaatactg ataggagaga ctattaagat tgtgattgaa gattatgtgc | 1140 |

-continued

```
aacacttgag tggctatcac ttcaaactga aatttgaccc agaactactt ttcaacaaac    1200
aattccagta ccaaaatcgt attgctgctg aatttaacac cctctatcac tggcatcccc    1260
ttctgcctga caccttttcaa attcatgacc agaaatacaa ctatcaacag tttatctaca   1320
acaactctat attgctggaa catggaatta cccagtttgt tgaatcattc accaggcaaa    1380
ttgctggcag ggttgctggt ggtaggaatg ttccacccgc agtacagaaa gtatcacagg    1440
cttccattga ccagagcagg cagatgaaat accagtcttt taatgagtac cgcaaacgct    1500
ttatgctgaa gccctatgaa tcatttgaag aacttacagg agaaaaggaa atgtctgcag    1560
agttggaagc actctatggt gacatcgatg ctgtggagct gtatcctgcc cttctggtag    1620
aaaagcctcg gccagatgcc atctttggtg aaaccatggt agaagttgga gcaccattct    1680
ccttgaaagg acttatgggt aatgttatat gttctcctgc ctactggaag ccaagcactt    1740
ttggtggaga agtgggtttt caaatcatca acactgcctc aattcagtct ctcatctgca    1800
ataacgtgaa gggctgtccc tttacttcat tcagtgttcc agatccagag ctcattaaaa    1860
cagtcaccat caatgcaagt tcttcccgct ccggactaga tgatatcaat cccacagtac    1920
tactaaaaga acgttcgact gaactgtaga agtctaatga tcatatttat ttatttatat    1980
gaaccatgtc tattaattta attatttaat aatatttata ttaaactcct tatgttactt    2040
aacatcttct gtaacagaag tcagtactcc tgttgcggag aaaggagtca tacttgtgaa    2100
gacttttatg tcactactct aaagattttg ctgttgctgt taagtttgga aaacagttt     2160
tattctgttt tataaaccag agagaaatga gttttgacgt cttttttactt gaatttcaac   2220
ttatattata agaacgaaag taagatgtt tgaatactta aacactatca caagatggca     2280
aaatgctgaa agttttttaca ctgtcgatgt ttccaatgca tcttccatga tgcattagaa   2340
gtaactaatg tttgaaattt taaagtactt ttggttatt ttctgtcatc aaacaaaaac     2400
aggtatcagt gcattattaa atgaatattt aaattagaca ttaccagtaa tttcatgtct    2460
acttttaaaa atcagcaatg aaacaataat ttgaaatttc taaattcata gggtagaatc    2520
acctgtaaaa gcttgtttga tttcttaaag ttattaaact tgtacatata ccaaaaagaa    2580
gctgtcttgg atttaaatct gtaaaatcag atgaaatttt actacaattg cttgttaaaa    2640
tatttttataa gtgatgttcc ttttttcacca agagtataaa cctttttagt gtgactgtta  2700
aaacttcctt ttaaatcaaa atgccaaatt tattaaggtg gtggagccac tgcagtgtta    2760
tctcaaaata agaatatttt gttgagatat tccagaattt gtttatatgg ctggtaacat    2820
gtaaaatcta tatcagcaaa agggtctacc tttaaaataa gcaataacaa agaagaaaac    2880
caaattattg ttcaaattta ggtttaaaact tttgaagcaa actttttttt atccttgtgc   2940
actgcaggcc tggtactcag attttgctat gaggttaatg aagtaccaag ctgtgcttga    3000
ataacgatat gttttctcag attttctgtt gtacagttta atttagcagt ccatatcaca    3060
ttgcaaaagt agcaatgacc tcataaaata cctcttcaaa atgcttaaat tcatttcaca    3120
cattaattt atctcagtct tgaagccaat tcagtaggtg cattggaatc aagcctggct     3180
acctgcatgc tgttcctttt cttttcttct tttagccatt ttgctaagag acacagtctt    3240
ctcatcactt cgtttctcct atttttgtttt actagtttta agatcagagt tcactttctt   3300
tggactctgc ctatattttc ttacctgaac ttttgcaagt tttcaggtaa acctcagctc    3360
aggactgcta tttagctcct cttaagaaga ttaaaagaga aaaaaaaagg cccttttaaa    3420
aatagtatac acttatttta agtgaaaagc agagaatttc atttatagct aattttagct    3480
```

-continued

```
atctgtaacc aagatggatg caaagaggct agtgcctcag agagaactgt acggggtttg    3540
tgactggaaa aagttacgtt cccattctaa ttaatgccct ttcttattta aaacaaaac     3600 caaatgatat ctaagtagtt ctcagcaata ataataatga cgataatact tcttttccac    3660
atctcattgt cactgacatt taatggtact gtatattact taatttattg aagattatta    3720
tttatgtctt attaggacac tatggttata aactgtgttt aagcctacaa tcattgattt    3780
ttttttgtta tgtcacaatc agtatatttt ctttggggtt acctctctga atattatgta    3840
aacaatccaa agaaatgatt gtattaagat ttgtgaataa attttagaa atctgattgg     3900 catattgaga tatttaaggt tgaatgtttg tccttaggat aggcctatgt gctagcccac    3960
aaagaatatt gtctcattag cctgaatgtg ccataagact gacctttaa aatgttttga     4020 gggatctgtg gatgcttcgt taatttgttc agccacaatt tattgagaaa atattctgtg    4080
tcaagcactg tgggttttaa tattttttaaa tcaaacgctg attacagata atagtattta    4140
tataaataat tgaaaaaaat tttcttttgg gaagagggag aaaatgaaat aaatatcatt    4200
aaagataact caggagaatc ttctttacaa ttttacgttt agaatgttta aggttaagaa    4260
agaaatagtc aatatgcttg tataaaacac tgttcactgt ttttttttaaa aaaaaaactt   4320 gatttgttat taacattgat ctgctgacaa aacctgggaa tttgggttgt gtatgcgaat    4380
gtttcagtgc ctcagacaaa tgtgtattta acttatgtaa aagataagtc tggaaataaa    4440
tgtctgttta ttttttgtact attta                                        4465
```

```
<210> SEQ ID NO 3
<211> LENGTH: 599
<212> TYPE: PRT
<213> ORGANISM: Homo sapiens

<400> SEQUENCE: 3

Met Ser Arg Ser Leu Leu Leu Arg Phe Leu Leu Phe Leu Leu Leu Leu
1               5                   10                  15

Pro Pro Leu Pro Val Leu Leu Ala Asp Pro Gly Ala Pro Thr Pro Val
                20                  25                  30

Asn Pro Cys Cys Tyr Tyr Pro Cys Gln His Gln Gly Ile Cys Val Arg
            35                  40                  45

Phe Gly Leu Asp Arg Tyr Gln Cys Asp Cys Thr Arg Thr Gly Tyr Ser
        50                  55                  60

Gly Pro Asn Cys Thr Ile Pro Gly Leu Trp Thr Trp Leu Arg Asn Ser
65                  70                  75                  80

Leu Arg Pro Ser Pro Ser Phe Thr His Phe Leu Thr His Gly Arg
                85                  90                  95

Trp Phe Trp Glu Phe Val Asn Ala Thr Phe Ile Arg Glu Met Leu Met
                100                 105                 110

Arg Leu Val Leu Thr Val Arg Ser Asn Leu Ile Pro Ser Pro Pro Thr
            115                 120                 125

Tyr Asn Ser Ala His Asp Tyr Ile Ser Trp Glu Ser Phe Ser Asn Val
        130                 135                 140

Ser Tyr Tyr Thr Arg Ile Leu Pro Ser Val Pro Lys Asp Cys Pro Thr
145                 150                 155                 160

Pro Met Gly Thr Lys Gly Lys Lys Gln Leu Pro Asp Ala Gln Leu Leu
                165                 170                 175

Ala Arg Arg Phe Leu Leu Arg Arg Lys Phe Ile Pro Asp Pro Gln Gly
            180                 185                 190

Thr Asn Leu Met Phe Ala Phe Phe Ala Gln His Phe Thr His Gln Phe
```

```
                    195                 200                 205
Phe Lys Thr Ser Gly Lys Met Gly Pro Gly Phe Thr Lys Ala Leu Gly
210                 215                 220

His Gly Val Asp Leu Gly His Ile Tyr Gly Asp Asn Leu Glu Arg Gln
225                 230                 235                 240

Tyr Gln Leu Arg Leu Phe Lys Asp Gly Lys Leu Lys Tyr Gln Val Leu
                245                 250                 255

Asp Gly Glu Met Tyr Pro Pro Ser Val Glu Ala Pro Val Leu Met
                260                 265                 270

His Tyr Pro Arg Gly Ile Pro Pro Gln Ser Gln Met Ala Val Gly Gln
                275                 280                 285

Glu Val Phe Gly Leu Leu Pro Gly Leu Met Leu Tyr Ala Thr Leu Trp
290                 295                 300

Leu Arg Glu His Asn Arg Val Cys Asp Leu Leu Lys Ala Glu His Pro
305                 310                 315                 320

Thr Trp Gly Asp Glu Gln Leu Phe Gln Thr Thr Arg Leu Ile Leu Ile
                325                 330                 335

Gly Glu Thr Ile Lys Ile Val Ile Glu Glu Tyr Val Gln Gln Leu Ser
                340                 345                 350

Gly Tyr Phe Leu Gln Leu Lys Phe Asp Pro Glu Leu Leu Phe Gly Val
                355                 360                 365

Gln Phe Gln Tyr Arg Asn Arg Ile Ala Met Glu Phe Asn His Leu Tyr
370                 375                 380

His Trp His Pro Leu Met Pro Asp Ser Phe Lys Val Gly Ser Gln Glu
385                 390                 395                 400

Tyr Ser Tyr Glu Gln Phe Leu Phe Asn Thr Ser Met Leu Val Asp Tyr
                405                 410                 415

Gly Val Glu Ala Leu Val Asp Ala Phe Ser Arg Gln Ile Ala Gly Arg
                420                 425                 430

Ile Gly Gly Gly Arg Asn Met Asp His His Ile Leu His Val Ala Val
                435                 440                 445

Asp Val Ile Arg Glu Ser Arg Glu Met Arg Leu Gln Pro Phe Asn Glu
450                 455                 460

Tyr Arg Lys Arg Phe Gly Met Lys Pro Tyr Thr Ser Phe Gln Glu Leu
465                 470                 475                 480

Val Gly Glu Lys Glu Met Ala Ala Glu Leu Glu Leu Tyr Gly Asp
                485                 490                 495

Ile Asp Ala Leu Glu Phe Tyr Pro Gly Leu Leu Leu Glu Lys Cys His
                500                 505                 510

Pro Asn Ser Ile Phe Gly Glu Ser Met Ile Glu Ile Gly Ala Pro Phe
                515                 520                 525

Ser Leu Lys Gly Leu Leu Gly Asn Pro Ile Cys Ser Pro Glu Tyr Trp
530                 535                 540

Lys Pro Ser Thr Phe Gly Gly Glu Val Gly Phe Asn Ile Val Lys Thr
545                 550                 555                 560

Ala Thr Leu Lys Lys Leu Val Cys Leu Asn Thr Lys Thr Cys Pro Tyr
                565                 570                 575

Val Ser Phe Arg Val Pro Asp Ala Ser Gln Asp Asp Gly Pro Ala Val
                580                 585                 590

Glu Arg Pro Ser Thr Glu Leu
                595

<210> SEQ ID NO 4
```

<211> LENGTH: 604
<212> TYPE: PRT
<213> ORGANISM: Homo sapiens

<400> SEQUENCE: 4

Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp
130                 135                 140

Cys Pro Thr Pro Leu Gly Val Lys Gly Lys Lys Gln Leu Pro Asp Ser
145                 150                 155                 160

Asn Glu Ile Val Glu Lys Leu Leu Leu Arg Arg Lys Phe Ile Pro Asp
                165                 170                 175

Pro Gln Gly Ser Asn Met Met Phe Ala Phe Ala Gln His Phe Thr
            180                 185                 190

His Gln Phe Phe Lys Thr Asp His Lys Arg Gly Pro Ala Phe Thr Asn
        195                 200                 205

Gly Leu Gly His Gly Val Asp Leu Asn His Ile Tyr Gly Glu Thr Leu
210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
            260                 265                 270

Val Gly Gln Glu Val Phe Gly Leu Val Pro Gly Leu Met Met Tyr Ala
        275                 280                 285

Thr Ile Trp Leu Arg Glu His Asn Arg Val Cys Asp Val Leu Lys Gln
290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
            340                 345                 350

Phe Asn Lys Gln Phe Gln Tyr Gln Asn Arg Ile Ala Ala Glu Phe Asn
        355                 360                 365

Thr Leu Tyr His Trp His Pro Leu Leu Pro Asp Thr Phe Gln Ile His
370                 375                 380

Asp Gln Lys Tyr Asn Tyr Gln Gln Phe Ile Tyr Asn Asn Ser Ile Leu

```
                385                 390                 395                 400
Leu Glu His Gly Ile Thr Gln Phe Val Glu Ser Phe Thr Arg Gln Ile
                    405                 410                 415

Ala Gly Arg Val Ala Gly Arg Asn Val Pro Pro Ala Val Gln Lys
                420                 425                 430

Val Ser Gln Ala Ser Ile Asp Gln Ser Arg Gln Met Lys Tyr Gln Ser
                    435                 440                 445

Phe Asn Glu Tyr Arg Lys Arg Phe Met Leu Lys Pro Tyr Glu Ser Phe
            450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                    485                 490                 495

Lys Pro Arg Pro Asp Ala Ile Phe Gly Glu Thr Met Val Glu Val Gly
                500                 505                 510

Ala Pro Phe Ser Leu Lys Gly Leu Met Gly Asn Val Ile Cys Ser Pro
                515                 520                 525

Ala Tyr Trp Lys Pro Ser Thr Phe Gly Gly Glu Val Gly Phe Gln Ile
            530                 535                 540

Ile Asn Thr Ala Ser Ile Gln Ser Leu Ile Cys Asn Asn Val Lys Gly
545                 550                 555                 560

Cys Pro Phe Thr Ser Phe Ser Val Pro Asp Pro Glu Leu Ile Lys Thr
                    565                 570                 575

Val Thr Ile Asn Ala Ser Ser Ser Arg Ser Gly Leu Asp Asp Ile Asn
                580                 585                 590

Pro Thr Val Leu Leu Lys Glu Arg Ser Thr Glu Leu
            595                 600

<210> SEQ ID NO 5
<211> LENGTH: 2757
<212> TYPE: DNA
<213> ORGANISM: Artificial sequence
<220> FEATURE:
<223> OTHER INFORMATION: Mouse COX-1 cDNA

<400> SEQUENCE: 5
gccgttggca ttgcacatcc atccactccc agagtcatga gtcgaaggag tctctcgctc      60
tggtttcccc tgctgctgct cctgctgctg ccgccgacac cctcggtcct gctcgcagat     120 cctgggggtgc cctcaccagt caatccctgt tgttactatc cgtgccagaa ccagggtgtc     180
tgtgtccgct ttggcctcga caactaccag tgtgattgta ctcgcacggg ctactcaggc     240
cccaactgta ccatccctga gatctggacc tggcttcgga attctctgcg gcccagcccc     300
tcgttcaccc atttcctgct gacacatgga tactggctct gggaatttgt gaatgccacc     360
ttcatccgag aagtactcat gcgcctggta ctcacagtgc ggtccaacct tatccccagc     420
cctccgacct acaactcagc gcatgactac atcagctggg agtccttctc caatgtgagc     480
tactatactc gcattctgcc ctctgtaccc aaagactgcc ccacacccat ggggaccaaa     540
gggaagaaac agttaccaga tgttcagctt ctggcccaac agctgctgct gagaagggag     600
ttcattcctg ccccccaggg caccaacatc ctgtttgcct tctttgcaca acacttcacc     660
caccagttct tcaagaccct ctggaaagatg ggtcctggct taccaaggc cttaggccac     720 ggggtagacc ttggccacat ttatggagat aatctggaac gacagtatca cctgcggctc     780
ttcaaggatg ggaaacttaa gtaccaggtg ctggacggag aggtgtaccc accttccgtg     840
```

```
gaacaggcgt ccgtgttgat gcgctaccca ccaggtgtcc cgcctgaaag gcagatggct      900
gtgggccagg aggtgtttgg gttgcttccg gggctgatgc tcttctccac gatctggctt      960
cgtgaacata accgcgtgtg cgacctgctg aaggaggagc atcccacgtg ggatgatgag     1020
cagctcttcc agaccactcg cctcatcctt ataggagaaa ccatcaaaat tgtcattgag     1080
gagtatgtgc agcacttgag tggctatttc ctgcagctca gtttgaccc ggagctgctg      1140
ttccgagccc agttccaata tcgaaaccgc atcgccatgg aatttaacca tctctatcac     1200
tggcatccac tcatgcccaa ctccttccaa gtgggctcac aagagtacag ctacgagcag     1260
tttttattta acacttctat gctggtggac tatgggggttg aggcactggt ggatgccttc    1320
tctcgccaga gggctggccg gattggtgga ggtaggaact ttgactatca tgttctgcat     1380
gtggctgtgg atgtcatcaa ggagtcccga gagatgcgcc tacagccctt caatgaatac     1440
cgaaagaggt ttggcttgaa gccttacacc tctttccagg agctcacagg agagaaggag     1500
atggctgctg agttggagga gctgtacggt gacatcgatg ctttagagtt ctacccgggg     1560
ttgctgctgg agaagtgcca gcccaactcc atctttggag aaagtatgat agagatgggg     1620
gctccctttt ccctcaaggg cctcctaggg aatcccatct gttccccaga gtactggaaa     1680
cccagcacgt tcggtggtga cgtgggcttc aaccttgtca acacagcctc actgaagaaa     1740
ctggtctgcc tcaacaccaa gacctgcccc tatgtttcct tccgtgtgcc agattaccct     1800
ggagatgacg ggtctgtctt agtgagacgc tccactgagc tctgagggag ctggaaagca     1860
gcctctggag ggaggagttt tgttcctgat gaagacaagt ccttgatgtg gttttcgtg      1920
gcttggcatt gtgagagctg atgctcacat ttgaaacttt gggtcttacc cttgcctaga     1980
aaattgtgat tttgccactt tcggatgttg aattctttgt taactaagaa agttagaagt     2040
ggttttgtct gcctcctcag aacttggctc tttgttggca actcagaaag tcagatttct     2100
ggttgatttg gaatataggc ttaaaacttt atattatagg gtagggtgtg gttgcacaca     2160
ccttaatccc agcacttgga aggcagaggc agttggatct ctgggagttt gaggccagtt     2220
tggcctatat agtgagttct aggccagcca tggatgcata gtgagactct ttctcaaaac     2280
aaacaaacaa acaaacaaac aaacaacttt tagaatgtag aattccgtaa aaaaaaaaa      2340
tcccttgaaa gttaatgggg tcctcaattt tcttcctaga attggaggc ctcttcagaa       2400
tgttgactat ctgacaggtg actcagaagg tcctgttcct ggtcaatgat ctataacatg     2460
ggccaaaaca ttcccaactt gaatgtctag aatgtggaat tggttcattt tcctgttcag     2520
tgaaatggac acagaacaaa agaacccagt gtccagcaag aattgccttg cccaaaccta     2580
cgtctacgcc aaaggtcaag gcagtaaggt gttcttggga gccacactta gactcttttcc    2640
aaagatgtgg agggaacaga tggactcatc tatgatcttg gttggaaacc accacagttc     2700
tatccccatc cagatctttg cttgtggcag ctgtttctca tgaagctaat aaaattc        2757
```

<210> SEQ ID NO 6
<211> LENGTH: 3986
<212> TYPE: DNA
<213> ORGANISM: Artificial sequence
<220> FEATURE:
<223> OTHER INFORMATION: Mouse COX-2 cDNA

<400> SEQUENCE: 6

```
agttgtcaaa ctgcgagcta agagcttcag gagtcagtca ggactctgct cacgaagaat       60
ctcagcactg catcctgcca gctccaccgc caccaccact gccacctccg ctgccacctc      120
tgcgatgctc ttccgagctg tgctgctctg cgctgccctg gggctcagcc aggcagcaaa     180
```

```
tccttgctgt tccaatccat gtcaaaaccg tggggaatgt atgagcacag gatttgacca    240
gtataagtgt gactgtaccc ggactggatt ctatggtgaa aactgtacta cacctgaatt    300
tctgacaaga atcaaattac tgctgaagcc caccccaaac acagtgcact acatcctgac    360
ccacttcaag ggagtctgga acattgtgaa caacatcccc ttcctgcgaa gtttaactat    420
gaaatatgtg ctgacatcca gatcatattt gattgacagt ccacctactt acaatgtgca    480
ctatggttac aaaagctggg aagccttctc caacctctcc tactacacca gggcccttcc    540
tccagtagca gatgactgcc caactcccat gggtgtgaag ggaaataagg agcttcctga    600
ttcaaaagaa gtgctggaaa aggttcttct acggagagag ttcatccctg accccaagg     660 ctcaaatatg atgtttgcat tctttgccca gcacttcacc catcagtttt tcaagacaga    720
tcataagcga ggacctgggt tcacccgagg actgggccat ggagtggact aaatcacat     780 ttatggtgaa actctggaca gacaacataa actgcgcctt ttcaaggatg gaaaattgaa    840
atatcaggtc attggtggag aggtgtatcc ccccacagtc aaagacactc aggtagagat    900
gatctaccct cctcacatcc ctgagaacct gcagtttgct gtggggcagg aagtctttgg    960
tctggtgcct ggtctgatga tgtatgccac catctggctt cgggagcaca acagagtgtg   1020
cgacatactc aagcaggagc atcctgagtg gggtgatgag caactattcc aaaccagcag   1080
actcatactc ataggagaga ctatcaagat agtgatcgaa gactacgtgc aacacctgag   1140
cggttaccac ttcaaaactca gtttgaccc agagctcctt ttcaaccagc agttccagta   1200
tcagaaccgc attgcctctg aattcaacac actctatcac tggcaccccc tgctgcccga   1260
caccttcaac attgaagacc aggagtacag cttcaaacag tttctctaca caaactccat   1320
cctcctggaa catggactca ctcagtttgt tgagtcattc accagacaga ttgctggccg   1380
ggttgctggg ggaagaaatg tgccaattgc tgtacaagca gtggcaaagg cctccattga   1440
ccagagcaga gagatgaaat accagtctct caatgagtac cgcaaacgct ctccctgaa    1500 gccgtacaca tcatttgaag aacttacagg agagaaggaa atggctgcag aattgaaagc   1560
cctctacagt gacatcgatg tcatggaact gtacccctgcc ctgctggtgg aaaaacctcg   1620
tccagatgct atctttgggg agaccatggt agagcttgga gcaccattct ccttgaaagg   1680
acttatggga aatcccatct gttctcctca atactgaag ccgagcacct ttggaggcga   1740 agtgggttt aagatcatca atactgcctc aattcagtct ctcatctgca ataatgtgaa   1800
ggggtgtccc ttcacttctt tcaatgtgca agatccacag cctaccaaaa cagccaccat   1860
caatgcaagt gcctcccact ccagactaga tgacattaac cctacagtac taatcaaaag   1920
gcgttcaact gagctgtaaa agtctactga ccatatttat ttatttatgt gaaggaattt   1980
aatttaatta tttaatattt atactgaatt tttttcatg taacatcttc cataacagaa   2040
ggcaatgttc ttgaacaatg ttacatttgt gaagattcct ccggtgtttg tcctttaaat   2100
atgtgttacc tgaaactgaa aggaaatcag cattcattcc tctacataag ccagtgagaa   2160
gggaaatgaa ttttgatatc tttatacttg aatttcagat catgaattag cttaacaaga   2220
accaaggaaa aatgtatgaa tatgtgagtg ttgttacaag atgaaaaatg ctgcaggtat   2280
caacactgtt ggttacactg tgtcttcttt acctatgata ggagcatgta atgtggaatt   2340
cgtcttaaat ccttgcatat ctttatctca tcaaacaaag gggtccaagt tcagttttaa   2400
ataagcattt aaggcagata ctgacaacaa tctcattttt ttaaaatgtt gtcttgagac   2460
aaataatttg aaatttctaa attgggacgt ttgaatcact tttgaaagct cttactttct   2520
```

```
taagctgtca ggtttgtacc gacatggagt aaacagctat cataaacgta aatctccaaa    2580
actagtagaa attatgtcat gattgatggt taagatacca tgtcagggat tgtctttct     2640 tagaagtagt gaaagctact tactatgaca atcagacctt ccttgtatgt caaaatgctg    2700
gtgtggaagg tggtggagcc cgtgctgctc tgtcttaact atgagtgtga gctttaaagc    2760
tcgttgatga gtggtagcca gcaaagccta gagcaacaaa agcgttctac aaggaacta    2820 accaagaaca aagaagggtt cccaattaaa gatcacattc agggttaaac ttccaaagga    2880
gacatcctga tcctggtttt gtgctggcct ggtactcagt aggttttgc tgtgaggtta     2940 aagacttgcc agggctgaac ttcgaaacag ttttctgtt gcacagtatg atgtaacagt     3000
ccatctctca atgcaatagg tatcagtggc ctcgtgagct tcttcacaat atttgatatg    3060
tcttccagcc cattgaacct ggactgcaga aggccccatg tcatgtgtga gctcagcctg    3120
gatgccagca tttgctgctc ctcttagttc cgtttctcgt ggtcacttta ctacgagaaa    3180
cgctgattgg gttttcgtag ctgtgttacc aggttttag tatcagaact attcttctt      3240 taacctctat tcatattttc tctacttgaa gttttacatt caggaaaacc tcagcgctca    3300
ggactactat gtacctcccc tttggaggga aaaattcatt tttaggtaaa aggcaaaaat    3360
tttttaaaaa tattttttat ttataattat atggaagggc cctaccaaga tgctagaaat    3420
atagggagtt cctgacaaga aatttccatt cttattctga agaattgctt tcttacttaa    3480
aaacaaagac agtttgtgag tagttctggg caatagggat aaatataaaa caataatgat    3540
gatcattttc tacatctcat tatcagctga ggtactgtat attactgaat ttattgaaga    3600
tagttatgtc ttttagacat tgttgttata aactatgttt aagcctacta caagtgtttc    3660 tttttttgcat tatgttggaa ttgatgtacc ttttttatga ttacctctct gaactatggt   3720
gtgaacaatc aaacaaaatg atgagattaa cgttcatgga taaattctaa gaaaactagt    3780 gtatttttt gaaaagtttg aagttagaac ttaggctgtt ggaatttacg cataaagcag     3840
actgcatagg atccaatatt gactgaccca agcatgttat aaagactgac attttagaca    3900
ttttgaaggc cctgtaagtg tttattaatt agttagaact taattgatta aaaaatatat    3960
ccaaagcact ataggcatta gaattc                                         3986

<210> SEQ ID NO 7
<211> LENGTH: 602
<212> TYPE: PRT
<213> ORGANISM: Mus musculus

<400> SEQUENCE: 7

Met Ser Arg Arg Ser Leu Ser Leu Trp Phe Pro Leu Leu Leu Leu
1               5                   10                  15

Leu Leu Pro Pro Thr Pro Ser Val Leu Leu Ala Asp Pro Gly Val Pro
                20                  25                  30

Ser Pro Val Asn Pro Cys Cys Tyr Tyr Pro Cys Gln Asn Gln Gly Val
            35                  40                  45

Cys Val Arg Phe Gly Leu Asp Asn Tyr Gln Cys Asp Cys Thr Arg Thr
        50                  55                  60

Gly Tyr Ser Gly Pro Asn Cys Thr Ile Pro Glu Ile Trp Thr Trp Leu
65                  70                  75                  80

Arg Asn Ser Leu Arg Pro Ser Pro Ser Phe Thr His Phe Leu Leu Thr
                85                  90                  95

His Gly Tyr Trp Leu Trp Glu Phe Val Asn Ala Thr Phe Ile Arg Glu
            100                 105                 110
```

```
Val Leu Met Arg Leu Val Leu Thr Val Arg Ser Asn Leu Ile Pro Ser
        115                 120                 125

Pro Pro Thr Tyr Asn Ser Ala His Asp Tyr Ile Ser Trp Glu Ser Phe
        130                 135                 140

Ser Asn Val Ser Tyr Tyr Thr Arg Ile Leu Pro Ser Val Pro Lys Asp
145                 150                 155                 160

Cys Pro Thr Pro Met Gly Thr Lys Gly Lys Lys Gln Leu Pro Asp Val
                165                 170                 175

Gln Leu Leu Ala Gln Gln Leu Leu Arg Arg Glu Phe Ile Pro Ala
        180                 185                 190

Pro Gln Gly Thr Asn Ile Leu Phe Ala Phe Ala Gln His Phe Thr
        195                 200                 205

His Gln Phe Phe Lys Thr Ser Gly Lys Met Gly Pro Gly Phe Thr Lys
        210                 215                 220

Ala Leu Gly His Gly Val Asp Leu Gly His Ile Tyr Gly Asp Asn Leu
225                 230                 235                 240

Glu Arg Gln Tyr His Leu Arg Leu Phe Lys Asp Gly Lys Leu Lys Tyr
                245                 250                 255

Gln Val Leu Asp Gly Glu Val Tyr Pro Pro Ser Val Glu Gln Ala Ser
        260                 265                 270

Val Leu Met Arg Tyr Pro Pro Gly Val Pro Glu Arg Gln Met Ala
        275                 280                 285

Val Gly Gln Glu Val Phe Gly Leu Leu Pro Gly Leu Met Leu Phe Ser
        290                 295                 300

Thr Ile Trp Leu Arg Glu His Asn Arg Val Cys Asp Leu Leu Lys Glu
305                 310                 315                 320

Glu His Pro Thr Trp Asp Asp Glu Gln Leu Phe Gln Thr Thr Arg Leu
                325                 330                 335

Ile Leu Ile Gly Glu Thr Ile Lys Ile Val Ile Glu Glu Tyr Val Gln
                340                 345                 350

His Leu Ser Gly Tyr Phe Leu Gln Leu Lys Phe Asp Pro Glu Leu Leu
                355                 360                 365

Phe Arg Ala Gln Phe Gln Tyr Arg Asn Arg Ile Ala Met Glu Phe Asn
        370                 375                 380

His Leu Tyr His Trp His Pro Leu Met Pro Asn Ser Phe Gln Val Gly
385                 390                 395                 400

Ser Gln Glu Tyr Ser Tyr Glu Gln Phe Leu Phe Asn Thr Ser Met Leu
                405                 410                 415

Val Asp Tyr Gly Val Glu Ala Leu Val Asp Ala Phe Ser Arg Gln Arg
                420                 425                 430

Ala Gly Arg Ile Gly Gly Gly Arg Asn Phe Asp Tyr His Val Leu His
        435                 440                 445

Val Ala Val Asp Val Ile Lys Glu Ser Arg Glu Met Arg Leu Gln Pro
450                 455                 460

Phe Asn Glu Tyr Arg Lys Arg Phe Gly Leu Lys Pro Tyr Thr Ser Phe
465                 470                 475                 480

Gln Glu Leu Thr Gly Glu Lys Glu Met Ala Ala Glu Leu Glu Glu Leu
                485                 490                 495

Tyr Gly Asp Ile Asp Ala Leu Glu Phe Tyr Pro Gly Leu Leu Leu Glu
                500                 505                 510

Lys Cys Gln Pro Asn Ser Ile Phe Gly Glu Ser Met Ile Glu Met Gly
        515                 520                 525

Ala Pro Phe Ser Leu Lys Gly Leu Leu Gly Asn Pro Ile Cys Ser Pro
```

```
                530                 535                 540
Glu Tyr Trp Lys Pro Ser Thr Phe Gly Gly Asp Val Gly Phe Asn Leu
545                 550                 555                 560

Val Asn Thr Ala Ser Leu Lys Lys Leu Val Cys Leu Asn Thr Lys Thr
                565                 570                 575

Cys Pro Tyr Val Ser Phe Arg Val Pro Asp Tyr Pro Gly Asp Asp Gly
                580                 585                 590

Ser Val Leu Val Arg Arg Ser Thr Glu Leu
                595                 600

<210> SEQ ID NO 8
<211> LENGTH: 604
<212> TYPE: PRT
<213> ORGANISM: Mus musculus

<400> SEQUENCE: 8

Met Leu Phe Arg Ala Val Leu Leu Cys Ala Ala Leu Gly Leu Ser Gln
1               5                   10                  15

Ala Ala Asn Pro Cys Cys Ser Asn Pro Cys Gln Asn Arg Gly Glu Cys
                20                  25                  30

Met Ser Thr Gly Phe Asp Gln Tyr Lys Cys Asp Cys Thr Arg Thr Gly
            35                  40                  45

Phe Tyr Gly Glu Asn Cys Thr Thr Pro Glu Phe Leu Thr Arg Ile Lys
    50                  55                  60

Leu Leu Leu Lys Pro Thr Pro Asn Thr Val His Tyr Ile Leu Thr His
65                  70                  75                  80

Phe Lys Gly Val Trp Asn Ile Val Asn Asn Ile Pro Phe Leu Arg Ser
                85                  90                  95

Leu Thr Met Lys Tyr Val Leu Thr Ser Arg Ser Tyr Leu Ile Asp Ser
                100                 105                 110

Pro Pro Thr Tyr Asn Val His Tyr Gly Tyr Lys Ser Trp Glu Ala Phe
            115                 120                 125

Ser Asn Leu Ser Tyr Tyr Thr Arg Ala Leu Pro Pro Val Ala Asp Asp
    130                 135                 140

Cys Pro Thr Pro Met Gly Val Lys Gly Asn Lys Glu Leu Pro Asp Ser
145                 150                 155                 160

Lys Glu Val Leu Glu Lys Val Leu Leu Arg Arg Glu Phe Ile Pro Asp
                165                 170                 175

Pro Gln Gly Ser Asn Met Met Phe Ala Phe Phe Ala Gln His Phe Thr
            180                 185                 190

His Gln Phe Phe Lys Thr Asp His Lys Arg Gly Pro Gly Phe Thr Arg
    195                 200                 205

Gly Leu Gly His Gly Val Asp Leu Asn His Ile Tyr Gly Glu Thr Leu
210                 215                 220

Asp Arg Gln His Lys Leu Arg Leu Phe Lys Asp Gly Lys Leu Lys Tyr
225                 230                 235                 240

Gln Val Ile Gly Gly Glu Val Tyr Pro Pro Thr Val Lys Asp Thr Gln
                245                 250                 255

Val Glu Met Ile Tyr Pro Pro His Ile Pro Glu Asn Leu Gln Phe Ala
            260                 265                 270

Val Gly Gln Glu Val Phe Gly Leu Val Pro Gly Leu Met Met Tyr Ala
    275                 280                 285

Thr Ile Trp Leu Arg Glu His Asn Arg Val Cys Asp Ile Leu Lys Gln
    290                 295                 300
```

```
-continued

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
            325                 330                 335

His Leu Ser Gly Tyr His Phe Lys Leu Lys Phe Asp Pro Glu Leu Leu
            340                 345                 350

Phe Asn Gln Gln Phe Gln Tyr Gln Asn Arg Ile Ala Ser Glu Phe Asn
            355                 360                 365

Thr Leu Tyr His Trp His Pro Leu Leu Pro Asp Thr Phe Asn Ile Glu
            370                 375                 380

Asp Gln Glu Tyr Ser Phe Lys Gln Phe Leu Tyr Asn Asn Ser Ile Leu
385                 390                 395                 400

Leu Glu His Gly Leu Thr Gln Phe Val Glu Ser Phe Thr Arg Gln Ile
            405                 410                 415

Ala Gly Arg Val Ala Gly Gly Arg Asn Val Pro Ile Ala Val Gln Ala
            420                 425                 430

Val Ala Lys Ala Ser Ile Asp Gln Ser Arg Glu Met Lys Tyr Gln Ser
            435                 440                 445

Leu Asn Glu Tyr Arg Lys Arg Phe Ser Leu Lys Pro Tyr Thr Ser Phe
450                 455                 460

Glu Glu Leu Thr Gly Glu Lys Glu Met Ala Ala Glu Leu Lys Ala Leu
465                 470                 475                 480

Tyr Ser Asp Ile Asp Val Met Glu Leu Tyr Pro Ala Leu Leu Val Glu
            485                 490                 495

Lys Pro Arg Pro Asp Ala Ile Phe Gly Glu Thr Met Val Glu Leu Gly
            500                 505                 510

Ala Pro Phe Ser Leu Lys Gly Leu Met Gly Asn Pro Ile Cys Ser Pro
            515                 520                 525

Gln Tyr Trp Lys Pro Ser Thr Phe Gly Gly Glu Val Gly Phe Lys Ile
            530                 535                 540

Ile Asn Thr Ala Ser Ile Gln Ser Leu Ile Cys Asn Asn Val Lys Gly
545                 550                 555                 560

Cys Pro Phe Thr Ser Phe Asn Val Gln Asp Pro Gln Pro Thr Lys Thr
            565                 570                 575

Ala Thr Ile Asn Ala Ser Ala Ser His Ser Arg Leu Asp Asp Ile Asn
            580                 585                 590

Pro Thr Val Leu Ile Lys Arg Arg Ser Thr Glu Leu
            595                 600
```

What is claimed is:

1. A method for treating a wound comprising the step of administering continuously for at least two weeks a therapeutically effective amount of a composition comprising a formulated cyclooxygenase-2 (COX-2) protein having the amino acid sequence of SEQ ID NO:4 to a patient with a skin, tendon, ligament, or bone wound so that COX-2 activity is increased.

2. The method of claim 1, wherein the composition is administered topically, orally, intravenously, nasally or locally.

3. The method of claim 1, wherein the wound comprises a broken bone, a fractured bone, a brittle bone, a skin lesion, damaged skin, a site of surgical orthopedic procedure, damaged tendon, or damaged ligament.

4. The method of claim 1, wherein the composition is administered continuously for at least four weeks.

5. The method of claim 1, wherein the composition is administered continuously for at least six weeks.

6. The method of claim 1, wherein the composition is administered directly to or proximal to the location of the wound.

7. A method for treating a wound comprising the step of administering continuously for at least two weeks at or proximal to the site of the wound a therapeutically effective amount of a composition comprising a formulated COX-2 protein having the amino acid sequence of SEQ ID NO:4 to a patient with a skin, tendon, ligament, or bone wound so that COX-2 activity is increased.

8. The method of claim 7, wherein the wound comprises a broken bone, a fractured bone, a brittle bone, a skin lesion, damaged skin, a site of surgical orthopedic procedure, damaged tendon, or damaged ligament.

9. The method of claim 7, wherein the composition is administered continuously for at least four weeks.

10. The method of claim 7, wherein the composition is administered continuously for at least six weeks.

11. The method of claim 1, wherein the COX-2 is encoded by the nucleotide sequence of SEQ ID NO :2.

12. The method of claim 7, wherein the COX-2 is encoded by the nucleotide sequence of SEQ ID NO: 2.

* * * * *